(12) United States Patent
Kamimura et al.

(10) Patent No.: US 11,485,644 B2
(45) Date of Patent: Nov. 1, 2022

(54) MWW TYPE ZEOLITE, METHOD FOR PRODUCING SAME, AND CRACKING CATALYST

(71) Applicants: Mitsui Mining & Smelting Co., Ltd., Tokyo (JP); NATIONAL UNIVERSITY CORPORATION TOTTORI UNIVERSITY, Tottori (JP); NATIONAL UNIVERSITY CORPORATION YOKOHAMA NATIONAL UNIVERSITY, Kanagawa (JP)

(72) Inventors: Yoshihiro Kamimura, Ibaraki (JP); Akira Endou, Ibaraki (JP); Yasuo Yamazaki, Tokyo (JP); Naonobu Katada, Tottori (JP); Satoshi Suganuma, Tottori (JP); Yoshihiro Kubota, Kanagawa (JP); Satoshi Inagaki, Kanagawa (JP)

(73) Assignees: Mitsui Mining & Smelting Co., Ltd., Tokyo (JP); NATIONAL UNIVERSITY CORPORATION TOTTORI UNIVERSITY, Tottori (JP); NATIONAL UNIVERSITY CORPORATION YOKOHAMA NATIONAL UNIVERSITY, Kanagawa (JP)

( * ) Notice: Subject to any disclaimer, the term of this patent is extended or adjusted under 35 U.S.C. 154(b) by 0 days.

(21) Appl. No.: 16/767,011

(22) PCT Filed: Nov. 28, 2018

(86) PCT No.: PCT/JP2018/043866
§ 371 (c)(1),
(2) Date: May 26, 2020

(87) PCT Pub. No.: WO2019/107448
PCT Pub. Date: Jun. 6, 2019

(65) Prior Publication Data
US 2021/0002140 A1 Jan. 7, 2021

(30) Foreign Application Priority Data
Nov. 28, 2017 (JP) .............................. JP2017-227678

(51) Int. Cl.
C01B 39/46 (2006.01)
C01B 39/48 (2006.01)
B01J 29/70 (2006.01)
B01J 37/10 (2006.01)
C07C 4/18 (2006.01)
B01J 35/02 (2006.01)

(52) U.S. Cl.
CPC ........... *C01B 39/48* (2013.01); *B01J 29/7038* (2013.01); *B01J 35/026* (2013.01); *B01J 37/10* (2013.01); *C01B 39/46* (2013.01); *C07C 4/18* (2013.01); *C01P 2002/72* (2013.01); *C01P 2004/22* (2013.01); *C07C 2529/70* (2013.01)

(58) Field of Classification Search
CPC ...... C01B 39/46; C01B 39/48; B01J 29/7038; B01J 35/002; B01J 35/026; B01J 37/10; C07C 4/18; C07C 2529/70; C01P 2002/72; C01P 2004/22
USPC .................... 502/60; 423/700, 702, 704, 709
See application file for complete search history.

(56) References Cited

U.S. PATENT DOCUMENTS

| 2007/0191657 A1 | 8/2007 | Lai et al. |
| 2008/0027256 A1 | 1/2008 | Roth et al. |
| 2008/0027260 A1 | 1/2008 | Lai et al. |
| 2011/0021855 A1 | 1/2011 | Lai et al. |

(Continued)

FOREIGN PATENT DOCUMENTS

| CN | 101489677 | 7/2009 |
| CN | 103508465 B | 7/2015 |

(Continued)

OTHER PUBLICATIONS

Corma et al., "Synthesis and characterization of the MCM-22 zeolite", Elsevier, 1995, Zeolites 15, pp. 2-8.
Camblor et al., "Synthesis and Structural Characterization of MWW Type Zeolite ITQ-1, the Pure Silica Analog of MCM-22 and SSZ-25", Journal of Physical Chemistry B, 1998, vol. 102, No. 1, pp. 44-51.

(Continued)

*Primary Examiner* — Elizabeth D Wood
(74) *Attorney, Agent, or Firm* — Rankin, Hill & Clark LLP

(57) ABSTRACT

Provided are the following: an MWW type zeolite which has many Brønsted acid sites when in the form of a proton type and which is highly suitable as a cracking catalyst for cumene; a method for producing same; and an application of same. The present invention provides an MWW type zeolite in which the ratio (B/A) of the peak intensity (B) attributable to tetracoordinate aluminum relative to the peak intensity (A) attributable to hexacoordinate aluminum is 2 or more in $^{27}$Al MAS NMR, when measured as an ammonium type. The present invention also provides a method for producing an MWW type zeolite, the method having a step for carrying out a hydrothermal synthesis reaction in the presence of: a seed crystal of an MWW type zeolite containing no organic structure-directing agent; and a reaction mixture containing a silica source, an alumina source, an alkali source, an organic structure-directing agent, and water. The reaction mixture satisfies the following molar ratio: $X/SiO_2 < 0.15$ (here, X denotes the number of moles of the organic structure-directing agent).

13 Claims, 16 Drawing Sheets

(56) References Cited

U.S. PATENT DOCUMENTS

| | | | |
|---|---|---|---|
| 2014/0194660 A1* | 7/2014 | Hwang | C10G 29/205 585/449 |
| 2017/0043327 A1 | 2/2017 | Johnson et al. | |
| 2018/0264445 A1 | 9/2018 | Onozuka et al. | |

FOREIGN PATENT DOCUMENTS

| | | |
|---|---|---|
| CN | 106115728 A | 11/2016 |
| JP | 2008-308387 A | 12/2008 |
| JP | 2009-526739 A | 7/2009 |
| JP | 2009-544567 A | 12/2009 |
| JP | 2009-544568 A | 12/2009 |
| JP | 2013-66884 A | 4/2013 |
| JP | 2017-508700 A | 3/2017 |
| WO | 2007/094937 A1 | 8/2007 |
| WO | 2007/094938 A1 | 8/2007 |
| WO | 2008/013639 A1 | 1/2008 |
| WO | 2008/013644 A1 | 1/2008 |
| WO | 2008/016477 A2 | 2/2008 |
| WO | 2015/112293 A1 | 7/2015 |
| WO | 2017/090751 A1 | 6/2017 |

OTHER PUBLICATIONS

Corma, "Sorption, diffusion and catalytic properties of zeolites containing 10- and 12-member ring pores in the same structure", Elesevier, 1998, Microporous and Mesoporous Materials 21, pp. 487-495.

Liu et al., "Synthesis, characterization, and catalytic properties of MWW zeolite with variable Si/Al ratios", Elsevier, 2006, Microporous and Mesoporous Materials 94, pp. 304-312.

Kolodziejski et al., "27Al and 29Si MAS NMR Study of Zeolite MCM-22", The Journal of Physical Chemistry, 1995, vol. 99, No. 18, pp. 7002-7008.

Saha et al., "Seeding on the Synthesis of MCM-22 (MWW) Zeolite by Dry-Gel Conversion Method and its Catalytic Properties on the Skeleton Isomerization and the Cracking of Hexane", Materials Transactions, 2005, vol. 46, No. 12, pp. 2651-2658.

Ravishankar et al., "Multinuclear MAS NMR Spectroscopic Study of the Zeolite, MCM-22", Journal of the Chemical Society Faraday Transactions, 1995, vol. 91, No. 19, pp. 3549-3552.

Extended European Search Report (EESR) dated Aug. 26, 2020 issued in the corresponding European Patent Application No. 18883427.9.

* cited by examiner

REFERENCE EXAMPLE 1 (SEED CRYSTAL, UNCALCINED)

REFERENCE EXAMPLE 1 (SEED CRYSTAL, CALCINED PRODUCT)

EXAMPLE 1 (UNCALCINED)

EXAMPLE 1 (CALCINED PRODUCT)

EXAMPLE 2 (UNCALCINED)

EXAMPLE 2 (CALCINED PRODUCT)

EXAMPLE 3 (UNCALCINED)

EXAMPLE 3 (CALCINED PRODUCT)

EXAMPLE 4 (UNCALCINED)

EXAMPLE 4 (CALCINED PRODUCT)

EXAMPLE 5 (UNCALCINED)

EXAMPLE 5 (CALCINED PRODUCT)

EXAMPLE 6 (UNCALCINED)

EXAMPLE 6 (CALCINED PRODUCT)

EXAMPLE 7 (CALCINED PRODUCT)

EXAMPLE 8 (CALCINED PRODUCT)

COMPARATIVE EXAMPLE 3

COMPARATIVE EXAMPLE 13

COMPARATIVE EXAMPLE 15

COMPARATIVE EXAMPLE 17

REFERENCE EXAMPLE 1 (SEED CRYSTAL, CALCINED PRODUCT)

EXAMPLE 1 (CALCINED PRODUCT)

EXAMPLE 1 (UNCALCINED PRODUCT)

EXAMPLE 1 (PRODUCT SUBJECTED TO NH4 EXCHANGE AFTER CALCINATION)

EXAMPLE 2 (CALCINED PRODUCT)

EXAMPLE 3 (CALCINED PRODUCT)

EXAMPLE 4 (CALCINED PRODUCT)

EXAMPLE 5 (CALCINED PRODUCT)

REFERENCE EXAMPLE 1 (CALCINED PRODUCT)

EXAMPLE 1 (SUBJECTED TO NH₄ EXCHANGE AFTER CALCINATION)

MWW TYPE ZEOLITE, METHOD FOR PRODUCING SAME, AND CRACKING CATALYST

CROSS-REFERENCE TO RELATED APPLICATIONS:

This application is a National Phase Application of International Application No. PCT/JP2018/043866, filed Nov. 28, 2018, which claims the priority of Japan Patent Application No. 2017-227678, filed Nov. 28, 2017. The present application claims priority from both applications and each of these applications is herein incorporated in their entirety by reference.

TECHNICAL FIELD

The present invention relates to an MWW-type zeolite having a particle shape different from that of existing MCM-22, a suitable method for producing the MWW-type zeolite, and a cracking catalyst containing the MWW-type zeolite.

BACKGROUND ART

Synthetic zeolites are crystalline aluminosilicates in a narrow sense and have angstrom-sized uniform pores due to their crystal structure. This feature allows synthetic zeolites to be used industrially as molecular sieve adsorbents that exclusively adsorb molecules having a specific size, as adsorptive separators that adsorb molecules having strong affinity, or as catalyst bases.

In the technical field of zeolites, MWW refers to a multilayer substance having two pore systems, i.e., a 10-membered oxygen ring and a 12-membered oxygen ring in a two-dimensional channel system. Examples of zeolites having this structure include MCM-22, ITQ-1, and SSZ-25. MWW-type zeolites are promising as catalysts for various hydrocarbon conversion reactions, for example, catalysts for catalytic cracking, hydrogenation cracking, dewaxing, alkylation, transalkylation, and formation of olefins and aromatic compounds.

To date, MWW-type zeolites have been produced only by a method using, for example, hexamethyleneimine (HMI) as an organic structure-directing agent (hereinafter, abbreviated as "OSDA") (refer to Patent Documents 1 and 2 and Non-Patent Documents 1 to 4). Therefore, it has been considered that the use of a large amount of OSDA is essential to obtain MWW-type zeolites.

Methods for synthesizing MWW-type zeolites are described in, for example, Patent Documents 1 and 2 and Non-Patent Documents 1 to 4. In a typical method, an organic substance such as hexamethyleneimine is used as an OSDA in the presence of sodium ions or potassium ions. However, the use of a large amount of an OSDA is essential for synthesizing MWW-type zeolites (HMI/$SiO_2$>0.15). Further, OSDAs are expensive, and, it is not advantageous to industrially use an OSDA. In addition, an OSDA will be incorporated in the crystal of a formed zeolite. Accordingly, in order to use the zeolite as an adsorbent or a catalyst, a large amount of an OSDA needs to be removed by calcining the zeolite. Exhaust gas formed in this stage may cause environmental pollution. Furthermore, in synthesizing a zeolite, a synthesis mother liquid containing a decomposition product from an OSDA will be discharged. This may cause environmental pollution, and a detoxifying treatment of the synthesis mother liquid requires a large amount of chemicals. As described above, the method for synthesizing an MWW-type zeolite using an OSDA is costly and environmentally unfriendly. Accordingly, it is desirable to realize a production method without using an OSDA or with using an OSDA at an amount as small as possible. Further, it is desirable to realize an MWW-type zeolite produced by the method.

Patent Document 1: Japanese Unexamined Patent Application (Translation of PCT Application), Publication No. 2009-544567 Patent Document 2: Japanese Unexamined Patent Application (Translation of PCT Application), Publication No. 2009-526739

Non-Patent Document 1: Zeolites, 1995,15, 2-8

Non-Patent Document 2: Journal of Physical Chemistry B, 1998, 102, 44-51

Non-Patent Document 3: Microporous and Mesoporous Materials, 1998, 21, 487-495

Non-Patent Document 4: Microporous and Mesoporous Materials, 2006, 94, 304-312

DISCLOSURE OF THE INVENTION

Problems to be Solved by the Invention

MWW-type zeolites obtained in the related art have a small number of Brønsted acid sites in the form of a proton type and do not have sufficient catalytic activity.

Furthermore, in the case where an MWW-type zeolite is synthesized in accordance with an existing document (for example, Non-Patent Document 1), a large amount of hexamethyleneimine, i.e., an OSDA, is necessary (HMI/$SiO_2$=0.5) for the synthesis of the MWW-type zeolite, which results in problematic environmental load and cost.

An object of the present invention is to provide an MWW-type zeolite capable of eliminating the drawbacks in the related art described above.

Another object of the present invention is to provide a method capable of producing, at a low cost without using an OSDA as much as possible, an MWW-type zeolite having physical properties different from those of an existing MWW-type zeolite synthesized by using a large amount of OSDA, the method being capable of reducing environmental load as much as possible.

Means for Solving the Problems

The present invention provides an MWW-type zeolite in which substantially all aluminum contained inside the framework is tetracoordinated.

The present invention further provides a method for producing an MWW-type zeolite, the method including a step of carrying out hydrothermal synthesis in the presence of a seed crystal of an MWW-type zeolite containing no OSDA, and a reaction mixture containing a silica source, an alumina source, an alkali source, an OSDA, and water, in which the reaction mixture satisfies a molar ratio below:

$X/SiO_2$<0.15 (where X denotes the number of moles of the OSDA).

Effects of the Invention

The MWW-type zeolite according to the present invention has a large number of Brønsted acid sites in the form of a proton type and is suitable as a cracking reaction catalyst for cumene. In the method for producing an MWW-type zeolite according to the present invention, the MWW-type zeolite can be efficiently produced at a low cost because an OSDA is used only in a very small amount. In addition, since an MWW-type zeolite is produced from a reaction mixture prepared by using only a very small amount of OSDA, the amount of OSDA discharge can be significantly reduced, and the environmental load is low.

PREFERRED MODE FOR CARRYING OUT THE INVENTION

Figure 1:
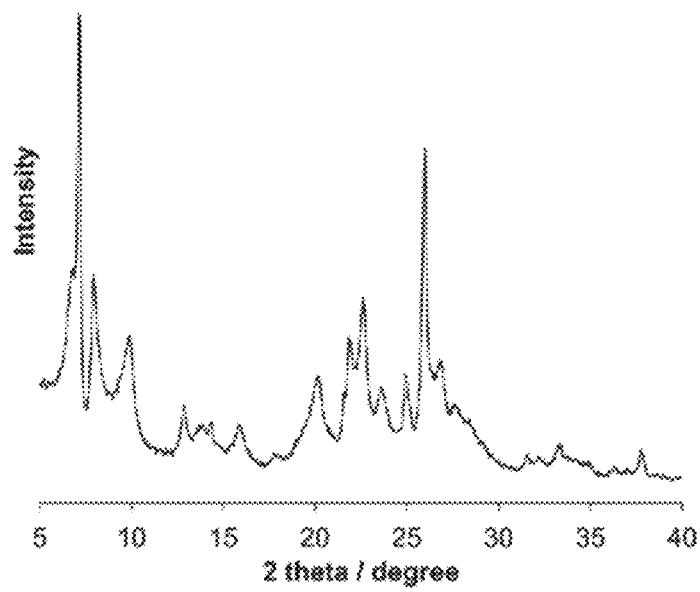
FIG. 1 is an X-ray diffraction pattern of an uncalcined MWW-type zeolite for a seed crystal, synthesized in Reference Example 1.

Hereafter, the present invention will be described on the basis of a preferred embodiment thereof. First, an MWW-type zeolite according to the present embodiment will be described. The MWW-type zeolite according to the present embodiment has an aluminosilicate framework.

Zeolites have a framework constituted by elements of Si, Al, and O. The periphery of an Al (aluminum) atom bound inside the framework is negatively charged. To compensate for the electric charge, a cationic substance such as an alkali metal ion, an alkaline earth metal ion, a transition metal ion, an ammonium ion, or a proton (hydrogen ion) can coordinate as a counter cation. For example, a zeolite having a sodium ion as a counter cation is referred to as a sodium type, a zeolite having a proton as a counter cation is referred to as a proton type, and a zeolite having an ammonium ion as a counter cation is referred to as an ammonium type. The counter cation can be exchanged for another cation, which exhibits an ion-exchange function. The MWW-type zeolite of the present embodiment may have any counter cation. In the case where the MWW-type zeolite of the present embodiment is produced by using a very small amount of an OSDA, as in a suitable production method described below, the MWW-type zeolite may be an MWW-type zeolite from which the OSDA is removed by calcination or alternatively an uncalcined MWW-type zeolite. In general, an ion that compensates for the negative charge of a tetracoordinate metal in the framework of an MWW-type zeolite after calcination and is present outside the framework is a cation such as a proton, a sodium cation, or an ammonium cation. Other substances existing in pores are only water or a small amount of adsorption gas.

In the MWW-type zeolite of the present embodiment, substantially all aluminum contained is preferably tetracoordinated. Specifically, in the MWW-type zeolite according to the present embodiment, a ratio (B/A) of a peak intensity (B) attributable to tetracoordinate aluminum to a peak intensity (A) attributable to hexacoordinate aluminum is preferably 2 or more in $^{27}Al$ MAS NMR, as measured in the form of, for example, an ammonium type.

Reactions that use a zeolite as a catalyst mostly utilize an acidic nature. Introduction of Brønsted acid sites into a zeolite is usually performed by ion-exchanging a positive ion ($Na^+$) in a pore of a sodium-type zeolite for $NH_4^+$, and subsequently calcining the resulting zeolite at 350° C. or higher to produce a proton-type zeolite having a crosslinked hydroxyl group (Si(OH)Al) in which Si and Al in the framework are crosslinked.

It is known that aluminum contained in a solid zeolite includes intra-framework aluminum having a Si—O—Al covalent bond and extra-framework aluminum that has no Si—O—Al covalent bond. Of these, with an increase in intra-framework aluminum, the ion exchange capacity increases. It is possible to perform ion exchange of 1 mole of a monovalent cation with 1 mole of aluminum. In addition, the introduction of Brønsted acid sites into a zeolite described above is performed through ion exchange from Na⁺ to $NH_4^+$. Accordingly, for these reasons, with an increase in the proportion of intra-framework aluminum in aluminum in the zeolite, the zeolite can have a larger number of Brønsted acid sites when the zeolite is converted into the proton type through ion exchange Thus, the resulting zeolite exhibits high activity as a catalyst. In principle, when aluminum is tetracoordinated, the aluminum is intra-framework aluminum. In contrast, hexacoordinate aluminum is extra-framework aluminum.

Accordingly, an MWW-type zeolite in which substantially all aluminum contained therein is tetracoordinated can exhibit an ion-exchange function very efficiently and is expected to have high activity because such a MWW-type zeolite has a large number of Brønsted acid sites in the form of a proton type.

The coordination state of aluminum can be analyzed by $^{27}Al$ MAS NMR. When the MWW-type zeolite of the present embodiment is a zeolite other than the ammonium type, such as the sodium type, measurement by $^{27}Al$ MAS NMR is performed after the zeolite is converted into the ammonium type through ion exchange. The ion exchange from a zeolite other than the ammonium type, such as the sodium type, to the ammonium type can be performed by the method described in Examples below. Analysis by $^{27}Al$ MAS NMR can also be performed by the method described in Examples below.

In the present specification, "substantially all aluminum contained is tetracoordinated" preferably means that in $^{27}Al$ MAS NMR as measured in the form of the ammonium type, a ratio of a peak intensity attributable to hexacoordinate aluminum to a peak intensity attributable to tetracoordinate aluminum is a certain value or less. In other words, a ratio of a peak intensity attributable to tetracoordinate aluminum to a peak intensity attributable to hexacoordinate aluminum is preferably a certain value or more. For example, when the intensity of a main peak among peaks attributable to hexacoordinate aluminum is denoted by A, and the intensity of a main peak among peaks attributable to tetracoordinate aluminum is denoted by B, B/A is preferably 2 or more, more preferably 10 or more, and particularly preferably 20 or more. Herein, the intensity ratio refers to a peak height ratio in an NMR chart. The main peak refers to a peak having the highest intensity (peak height).

Most preferably, in the MWW-type zeolite of the present embodiment, peaks attributable to tetracoordinate aluminum are solely observed and no peak attributable to hexacoordinate aluminum is observed as peaks attributable to aluminum in $^{27}Al$ MAS NMR when the zeolite is measured in the form of the ammonium type.

In $^{27}Al$ MAS NMR, for example, when aluminum nitrate of 1,000 ppm is used as a reference, peaks attributable to tetracoordinate aluminum are observed from 40 to 80 ppm, and peaks attributable to hexacoordinate aluminum are observed from −10 to 10 ppm.

In the MWW-type zeolite of the present embodiment, an amount of Brønsted acid sites with an adsorption heat of ammonia of 106 kJ/mol or more is preferably 0.5 mmol/g or more.

The amount of Brønsted acid sites with an adsorption heat of ammonia of a specific value or more can be measured by an $NH_3$-IRMS-TPD method. According to observation with an infrared spectrometer, ammonia adsorbed onto a Brønsted acid site becomes $NH_4^+$, and ammonia adsorbed onto a Lewis acid site becomes $NH_3$. Next, the temperature of a sample is increased to perform desorption of adsorbed ammonia. The temperature at which $NH_4^+$ and $NH_3$ consequently decrease is observed with an infrared spectrometer. At the same time, the ammonia concentration in the gas is measured with a mass spectrometer. With this method, it is possible to determine the number (amount of acid sites), type of each acid site present (type), and strength of each acid site present (strength). For example, a spectrum (TPD curve) of an amount of Brønsted acid sites with respect to a temperature can be obtained on the basis of a sample temperature, the type of ammonia detected at the temperature, and the concentration of the ammonia. A spectrum (TPD curve) of an amount of Brønsted acid sites with respect to adsorption heat of ammonia can also be obtained. The adsorption heat of ammonia refers to ammonia desorption energy that is derived from an equilibrium reaction formula relating to adsorption and desorption of ammonia on a solid acid catalyst. The strength of an acid site is represented by the adsorption heat of ammonia. That is, an adsorption point at which ammonia is strongly adsorbed is a strong acid site. Accordingly, a high adsorption heat of ammonia means a strong acid site. Thus, the amount of Brønsted acid sites with adsorption heat of ammonia of a specific value or more represents the amount of acid sites having a certain strength or more.

The amount of Brønsted acid sites of the MWW-type zeolite of the present embodiment is preferably 0.6 mmol/g or more, still more preferably 0.7 mmol/g or more, and most preferably 0.76 mmol/g or more. An MWW-type zeolite having such a high amount of Brønsted acid sites has not been obtained to date.

In the case where an MWW-type zeolite has a structure other than an ammonium type, such as a sodium type, the amount of Brønsted acid sites with an adsorption heat of ammonia of 106 kJ/mol or more is measured after the MWW-type zeolite is converted into an ammonium type through ion exchange. This ion exchange can be specifically performed by the method described in Examples. In the $NH_3$-IRMS-TPD method, prior to adsorbing ammonia, a zeolite sample is calcined at 550° C. for about 1 hour in oxygen flow to protonate the ammonium-type zeolite thereby, and is subjected to an ammonia adsorption.

The amount of Brønsted acid sites can be specifically measured by the method described in Examples below.

The MWW-type zeolite of the present embodiment preferably has a $SiO_2/Al_2O_3$ molar ratio of 200 or less. In addition to the feature that substantially all aluminum in the framework is tetracoordinated, such a high amount of aluminum in the zeolite can further enhance the activity of the MWW-type zeolite of the present embodiment. The $SiO_2/Al_2O_3$ molar ratio is more preferably 100 or less, particularly preferably 40 or less, and even more particularly preferably 37 or less. The lower limit of the $SiO_2/Al_2O_3$ molar ratio is not particularly limited. However, the ratio is preferably, for example, 5 or more, particularly preferably 10 or more, even more particularly preferably 17 or more in view of the manufacturability of the MWW-type zeolite. The $SiO_2/Al_2O_3$ molar ratio can be evaluated by, for example, ICP-AES composition analysis.

In the MWW-type zeolite of the present embodiment, an $Na_2O/Al_2O_3$ molar ratio in the form of the sodium type is preferably 0.05 or more because of a large amount of ion exchange resulting from the feature that substantially all aluminum contained is tetracoordinate aluminum. From this point of view, the $Na_2O/Al_2O_3$ molar ratio is more preferably 0.10 or more, and particularly preferably 0.30 or more. In the MWW-type zeolite, the $Na_2O/Al_2O_3$ molar ratio in the form of the sodium type is not particularly limited but is preferably 1 or less in theory. An exemplified method for converting an MWW-type zeolite into the sodium type includes placing 1 g of a zeolite other than the sodium type, such as the proton type or the ammonium type, in a 1 M NaNO$_3$ aqueous solution, and stirring it at 60° C. for 8 to 16 hours, followed by filtration, washing with water, and drying at 60° C.

The MWW-type zeolite of the present embodiment preferably has a micropore volume of 0.07 cm$^3$/g or more, which can enhance the activity of a catalyst. From this point of view, the micropore volume is more preferably 0.16 cm$^3$/g or more, and particularly preferably 0.19 cm$^3$/g or more. A larger micropore volume is preferred, but the upper limit of the micropore volume is, for example, 0.2530 cm$^3$/g or less in terms of theoretical value.

The micropore volume refers to a value measured for a state after an MWW-type zeolite of the sodium type is changed into the ammonium type through substitution. However, even for the MWW-type zeolite of the sodium type, the micropore volume measured is also preferably in the same range. The sodium-type zeolite can be obtained by, for example, the method described above. The micropore volume of the MWW-type zeolite of the sodium type can be measured by the method described in Examples below. Changing an MWW-type zeolite into the ammonium type through substitution and measuring the micropore volume after the substitution can be performed by the methods described in Examples below.

The MWW-type zeolite of the present embodiment preferably has a structure different from that of existing pillared MCM-22 in terms of X-ray diffraction pattern obtained by X-ray diffraction measurement. This X-ray diffraction measurement is performed for the as-synthesized, i.e., uncalcined, MWW-type zeolite of the present embodiment. As described in Examples below, an existing as-synthesized MWW-type zeolite has the structure of pillared MCM-22 in the uncalcined state. The X-ray diffraction pattern of the MWW-type zeolite of the present embodiment preferably has a peak in any range of 2θ=6.4° to 7.4°, 13.5° to 14.5°, 24.1° to 25.1°, 24.7 to 25.7°, 27.1 to 28.1°, 28.0° to 29.0°, 28.6° to 29.6°, and 29.1° to 30.1°, more preferably has peaks in two, three or more of these ranges, and most preferably has peaks in each of these ranges.

The MWW-type zeolite of the present embodiment may be an as-synthesized uncalcined product or alternatively a calcined product after synthesis. The 2θ-ranges where the peaks appear do not significantly change before and after calcination. Accordingly, the MWW-type zeolite of the present embodiment may be a calcined product of an MWW-type zeolite having peaks in the above specific ranges.

The MWW-type zeolite of the present embodiment preferably has a hexagonal plate-like shape (appearance). Such an MWW-type zeolite is considered to have high crystallinity and have a larger number of Brønsted acid sites. This particle shape (appearance) can be identified by observing the MWW-type zeolite with an ultra-high resolution field-emission scanning electron microscope. The magnification during observation is 20,000 or more and 200,000 or less.

One side of the hexagon of a hexagonal plate is preferably 0.001 μm or more and 1 μm or less, and more preferably 0.01 μm or more and 0.7 μm or less. The thickness of the plate is preferably 0.001 μm or more and 0.1 μm or less, and more preferably 0.02 μm or more and 0.1 μm or less. These dimensions are determined as the averages of 100 particles selected at random.

The hexagon in the hexagonal plate-like shape may be a regular hexagon but is not necessarily a regular hexagon. The hexagonal shape may be, for example, a shape formed by joining hexagons to each other. The hexagonal plate-like shape is preferably a flat-plate shape but includes a slightly curved plate shape. When the MWW-type zeolite is observed at a magnification in the above range, at least one of the observed particles may have a hexagonal plate-like shape, and all the observed particles of the MWW-type zeolite need not have a hexagonal plate-like shape.

In the present specification, the expression "an MWW-type zeolite has a hexagonal plate-like shape" means that the hexagonal plate-like shape is observed by the method described above in the case where the MWW-type zeolite is a sodium type product calcined after synthesis. However, the inventors believe that the hexagonal plate-like shape of the MWW-type zeolite of the present embodiment does not basically depend on the type of counter cation and whether calcination is performed after synthesis or not.

The MWW-type zeolite of the present embodiment is useful as various solid acid catalysts by unitizing the characteristic that aluminum in the zeolite is substantially constituted by tetracoordinate aluminum. For example, when the MWW-type zeolite of the present embodiment is used as a cracking catalyst for cumene, a high amount of consumption of cumene is exhibited.

A decomposition reaction (dealkylation) of cumene (IUPAC name: 2-phenylpropane or (1-methylethyl)benzene) shown in formula (1) below is considered to proceed on Brønsted acid sites and is widely carried out for evaluating Brønsted acid catalytic activity of a solid catalyst. In the cracking reaction of cumene described in Examples below, the cumene conversion rate of the MWW-type zeolite of the present embodiment is five times or more that of an MWW-type zeolite (calcined product) obtained in the related art.

$$C_6H_5-CH(CH_3)_2 \rightarrow C_6H_6 + C_3H_6 \quad (1)$$

MWW-type zeolites are also known as catalysts for producing cumene and ethylbenzene. These catalysts are useful for producing cumene by isopropylation of benzene and useful for similarly producing ethylbenzene by ethylation of benzene. A catalyst that promotes a certain reaction also promotes its reverse reaction. Therefore, a high activity for decomposition of cumene indicates a possible high activity for the reverse reaction, e.g., production of cumene and production of similar ethylbenzene.

To obtain the MWW-type zeolite of the present embodiment having the preferred features described above, a preferred production method described below is employed.

The present production method is a method for producing an MWW-type zeolite, the method including a step of carrying out hydrothermal synthesis in the presence of a seed crystal of an MWW-type zeolite containing no OSDA, and a reaction mixture containing a silica source, an alumina source, an alkali source, an OSDA, and water, in which the reaction mixture satisfies the following molar ratio:

X/SiO$_2$<0.15 (where X denotes the number of moles of the OSDA).

X/SiO$_2$ is preferably 0.01 or more.

One feature of the present production method lies in that a reaction mixture is prepared by adding a small amount of an OSDA composed of an organic compound. More specifically, an aqueous aluminosilicate gel containing sodium ions and a small amount of an OSDA is used as the reaction mixture. The presence of sodium ions and a small amount of an OSDA in the reaction mixture of the aqueous aluminosilicate gel is an essential condition. The presence of alkali metal ions other than sodium ions, such as lithium ions and potassium ions, is not essential in the production method according to the present invention. However, the use of alkali metal ions other than sodium ions is not excluded in the production method according to the present invention. Hexamethyleneimine is preferably used as the OSDA.

Another feature of the present production method lies in the use of a seed crystal containing no OSDA. The seed crystal used can be an MWW-type zeolite produced by the existing method, that is, the method using an OSDA. Since an as-produced seed crystal (MWW-type zeolite) obtained by the existing method contains an OSDA, an MWW-type zeolite obtained by removing the OSDA by calcination is used as the seed crystal. The calcination temperature is, for example, 500° C. to 800° C. The method for synthesizing an MWW-type zeolite in accordance with the existing method is described in, for example, Patent Documents 1 and 2 and Non-Patent Documents 1 to 4 mentioned above and is well known to those skilled in the art. There is no limitation of the type of OSDA used in the method for synthesizing an MWW-type zeolite in accordance with the existing method. In general, the use of hexamethyleneimine as the OSDA enables an MWW-type zeolite to be successfully produced particularly under the condition that an $HMI/SiO_2$ of a starting reaction mixture is 0.5 or more. Alternatively, the seed crystal used may be prepared by calcining an MWW-type zeolite obtained in accordance with the suitable method for producing an MWW-type zeolite according to the present invention described below.

A $SiO_2/Al_2O_3$ molar ratio of the seed crystal is preferably 10 to 40, and more preferably 15 to 25 in the case which utilizes an MWW-type zeolite obtained in accordance with the existing method, or an MWW-type zeolite obtained in accordance with the suitable method for producing an MWW-type zeolite according to the present invention as the seed crystal.

The amount of the seed crystal added is preferably in the range of 1% to 50% by mass, and more preferably in the range of 5% to 20% by mass relative to $SiO_2$ in the reaction mixture. A smaller amount of the seed crystal is preferred, provided that the amount of addition is within the above range. The amount of addition is determined in consideration of, for example, reaction rates and effects of reducing impurities.

The reaction mixture, to which the seed crystal is to be added, is preferably prepared by mixing a silica source, an alumina source, an alkali source, and water so as to have a composition represented by the molar ratios below. If the composition of the reaction mixture is out of this range, it is difficult to obtain a desired MWW-type zeolite.

$SiO_2/Al_2O_3$=5 or more and 200 or less
$Na_2O/SiO_2$=0.05 or more and 0.5 or less
$H_2O/SiO_2$=5 or more and 200 or less
$X/SiO_2$=0.01 or more and 0.15 or less, preferably 0.01 or more and less than 0.15 (where X denotes the number of moles of the organic structure-directing agent.)

More preferably, the reaction mixture has a composition represented by the molar ratios below.

$SiO_2/Al_2O_3$=60 or more and 100 or less
$Na_2O/SiO_2$=0.15 or more and 0.275 or less
$H_2O/SiO_2$=20 or more and 50 or less
$HMI/SiO_2$=0.01 or more and 0.05 or less The silica source used to obtain the reaction mixture having the above molar ratio may be a silicon source described below. Examples of the silicon source include silica and silicon-containing compounds capable of producing a silicate ion in water. Specifically, examples thereof include wet process silica, dry process silica, colloidal silica, and sodium silicate. Of these silica sources, silica (silicon dioxide) is preferably used from the viewpoint that a desired zeolite can be obtained without producing unnecessary by-products.

The alkali source may be, for example, sodium hydroxide. In the case where sodium aluminate is used as the alumina source, sodium, which is an alkali metal component contained therein, is simultaneously considered as NaOH and also functions as an alkali component. Accordingly, the Na described above is calculated as the sum of all the alkali components in the reaction mixture.

The alumina source may be an aluminum source described below. The aluminum source may be, for example, a water-soluble aluminum-containing compound or a powdery aluminum. Examples of the water-soluble aluminum-containing compound include sodium aluminate, aluminum nitrate, and aluminum sulfate. Aluminum hydroxide is also one of suitable aluminum sources. Alternatively, aluminosilicate gel, aluminosilicate zeolite, and the like can also be used. Of these aluminum sources, powdery aluminum, sodium aluminate, aluminum hydroxide, or aluminosilicate zeolite is preferably used from the viewpoint that a desired zeolite can be obtained without producing unnecessary by-products (such as a sulfate and a nitrate).

Regarding the addition order of the raw materials in preparation of the reaction mixture, a method with which a uniform reaction mixture is easily obtained may be employed. For example, a uniform reaction mixture can be obtained by adding an alumina source and an alkali source to water and dissolving them at room temperature, subsequently adding a silica source, and mixing with stirring. A seed crystal is added before the addition of the silica source or after mixing with the silica source. Subsequently, the resulting mixture is mixed and stirred so as to uniformly disperse the seed crystal. The temperature during preparation of the reaction mixture is also not particularly limited.

A seed crystal calcined product is added to the reaction mixture. The reaction mixture containing the seed crystal and a small amount of OSDA is placed in a hermetically sealed container and allowed to react by heating to crystallize an MWW-type zeolite under self-generated pressure. The seed crystal used can be obtained by the method described in any of Patent Documents 1 and 2 and Non-Patent Documents 1 to 4.

During crystallization of the reaction mixture containing the seed crystal by heating, the reaction mixture may be stirred in order to keep uniform temperature of the reaction mixture. The stirring can be performed by mixing with a stirring blade or rotating the container. The stirring intensity or the number of rotations may be adjusted according to the uniformity of the temperature and the degree of impurity by-production. The stirring may be performed either constantly or intermittently.

Heating is performed in a hermetically sealed state in either case where crystallization is performed under a stationary state or with stirring. The heating temperature is preferably 80° C. to 200° C., more preferably 100° C. to 180° C., and particularly preferably 140° C. to 170° C. This heating is performed under self-generated pressure. At a temperature of lower than 80° C., the production efficiency of the MWW-type zeolite is poor due to an excessively low crystallization rate. On the other hand, a temperature higher than 200° C. results in an increased production rate of impurities, together with an economically poor efficiency due to a requisite autoclave with a high pressure capacity. The heating time is not critical in the present production method. Heating may be performed until the production of an MWW-type zeolite having sufficiently high crystallinity.

An MWW-type zeolite having a satisfied crystallinity can be produced by heating typically about 80 hours or more, particularly preferably 90 hours or more, and even more particularly preferably 96 hours or more.

A crystal of the MWW-type zeolite can be obtained by the heating described above. After heating, the produced crystal powder is separated from a mother liquid by filtration, then washed with water or hot water, and dried. A small amount of OSDA remains in the product after drying, and therefore, calcination is performed at 500° C. to 800° C. The MWW-type zeolite obtained in this manner can be used as, for example, an adsorbent. When the MWW-type zeolite is used as a solid acid catalyst, for example, $Na^+$ ions in the crystal are exchanged for $NH_4^+$ ions, and the MWW-type zeolite can then be used as an $NH_4^+$ type (ammonium type). The ion exchange from $Na^+$ ions to $NH_4^+$ ions is preferably performed after the OSDA is removed by calcination.

An ammonium compound is used for ion exchange of the MWW-type zeolite synthesized in accordance with the present production method. For example, ammonium nitrate, ammonium chloride, ammonium acetate, or ammonium sulfate is preferably used as the ammonium compound. In the case where the ion exchange is performed by using an ammonium compound such as ammonium nitrate or ammonium chloride, a specific procedure preferably includes, for example, adding 100 to 1,000 mL of an aqueous solution having an ammonium ion concentration of 0.1 to 10 mol/L to about 2 g of the MWW-type zeolite after calcination. The pH of the ammonium ion-containing aqueous solution is preferably adjusted to around neutral. The ion exchange can be performed under heating or without heating the ammonium ion-containing aqueous solution. In the case of heating the ammonium ion-containing aqueous solution, the heating temperature is preferably 40° C. to 100° C. The MWW-type zeolite is dispersed in the ammonium ion-containing aqueous solution to prepare a dispersion liquid, and this state is held for a predetermined time to perform ion exchange. The holding time is preferably 0.5 to 48 hours. The dispersion liquid may be allowed to stand or may be stirred.

After the dispersion liquid is held for the predetermined time, the dispersion liquid is filtered to separate the MWW-type zeolite, and the MWW-type zeolite was washed with water. A combination of the above-described ion exchange treatment and washing with water may be performed multiple times as required. After the ion exchange treatment is performed in this manner, the MWW-type zeolite is dried to obtain an MWW-type zeolite of the $NH_4^+$ type. This MWW-type zeolite of the $NH_4^+$ type consequently has a significantly reduced alkali metal ion content.

The MWW-type zeolite obtained by the present production method can be suitably used as, for example, adsorptive separators in various industrial fields and various catalysts for hydrocarbon conversion reactions in the petrochemical industry. Examples of the hydrocarbon conversion reactions include catalytic cracking, hydrogenation cracking, dewaxing, alkylation, transalkylation, and formation and isomerization of olefins and aromatic compounds.

EXAMPLES

Hereafter, the present invention will be described in more detail by way of Examples. The scope of the present invention is not limited to the Examples. Herein, "%" means "% by mass" unless otherwise specified. Analytical instruments used in Examples and Comparative Examples below are as follows.

Powder X-ray diffractometer: D8 Advance, manufactured by Bruker AXS GmbH
Composition analyzer: ICP-AES LIBERTY Series II, manufactured by Varian, Inc.
Ultra-high resolution field-emission scanning electron microscope: SU9000, manufactured by Hitachi High-Tech Corporation
Solid-state $^{27}Al$ MAS NMR measuring apparatus: Bruker AVANCE-400, manufactured by Bruker-BioSpin Inc.
$N_2$ adsorption-desorption measuring apparatus: BELSORP-mini, manufactured by MicrotracBEL Corp.
Ammonia infrared-mass spectroscopy temperature-programmed desorption ($NH_3$-IRMS-TPD) analyzer: IRMS-TPD, manufactured by MicrotracBEL Corp.

Reference Example 1

Synthesis of Seed Crystal

Figure 2:
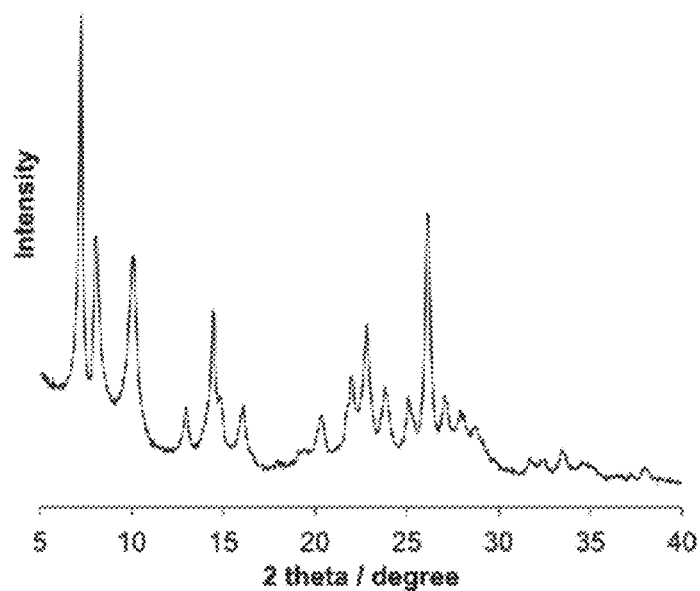
FIG. 2 is an X-ray diffraction pattern of a calcined MWW-type zeolite for a seed crystal, synthesized in Reference Example 1.

A seed crystal was synthesized in accordance with the method described in Non-Patent Document 1. An MWW-type zeolite (hereinafter, also referred to as "pillared MCM-22") was synthesized by using hexamethyleneimine as an OSDA, sodium aluminate as an alumina source, and fumed silica (Cab-O-Sil, M5) as a silica source and heating at 150° C. for 168 hours with stirring at 20 rpm. FIG. 1 shows an X-ray diffraction pattern of the (uncalcined) product obtained after washing, collecting, and drying. This crystal was calcined in an air atmosphere at 650° C. for 10 hours and subjected to composition analysis. The result showed that $SiO_2/Al_2O_3$ molar ratio was 20 and $Na_2O/Al_2O_3$ molar ratio was 0.042. FIG. 2 shows an X-ray diffraction pattern after calcination. The crystal of the MWW-type zeolite after calcination (hereinafter, also referred to as "3D MCM-22") was used as a seed crystal in Examples 1 to 8 described below.

Example 1

Synthesis of MWW-Type Zeolite 0.029 g of sodium aluminate and 0.538 g of a 50 w/v % sodium hydroxide were dissolved into 8.822 g of pure water to prepare an aqueous solution. Subsequently, 0.612 g of fumed silica (Cab-O-Sil, M5) was added to the aqueous solution gradually and mixed and stirred to prepare a gel having a composition shown in Table 1. This gel had a composition that could produce an amorphous substance and a mordenite-type zeolite if this gel was solely used to synthesize a zeolite (refer to Comparative Examples 1 to 4).

Figure 3:
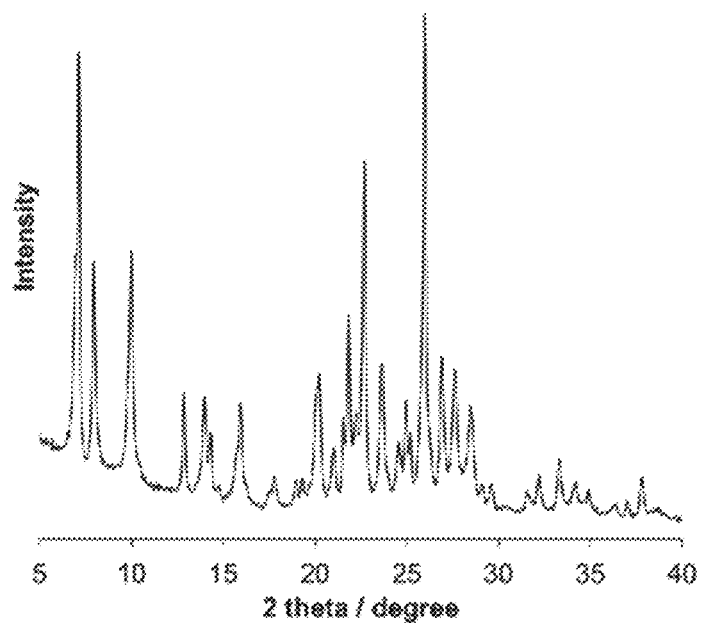
FIG. 3 is an X-ray diffraction pattern of an uncalcined product obtained in Example 1.

To the gel prepared as described above, 0.05 g of HMI and 0.122 g of the seed crystal calcined product were added, and the resulting gel was placed in a 23 cc hermetically sealed container made of stainless steel and allowed to stand under heating at 160° C. for 90 hours under self-generated pressure without stirring. The amount of the seed crystal added was 20% by mass relative to the silica component in the gel. After the hermetically sealed container was cooled, the resulting product was filtered and washed with water to obtain a white powder. FIG. 3 shows an X-ray diffraction pattern of this product. This product was confirmed to be an MWW-type zeolite containing no impurities. As one feature of the MWW-type zeolite synthesized by this production method, new peaks were observed at 2θ=6.96°, 13.97°, 24.56°, 25.18°, 27.61°, 28.46°, 29.08°, and 29.58° in the stage of the uncalcined product.

Figure 4:
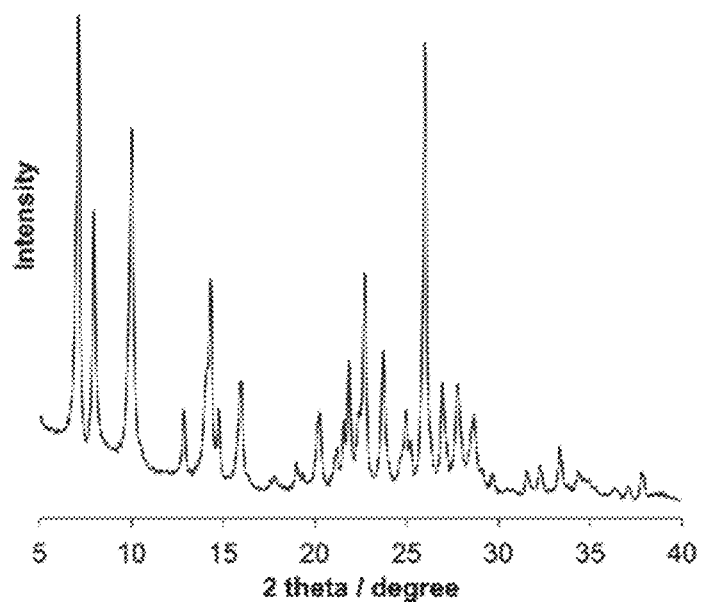
FIG. 4 is an X-ray diffraction pattern of a calcined product obtained in Example 1.
Figure 5:
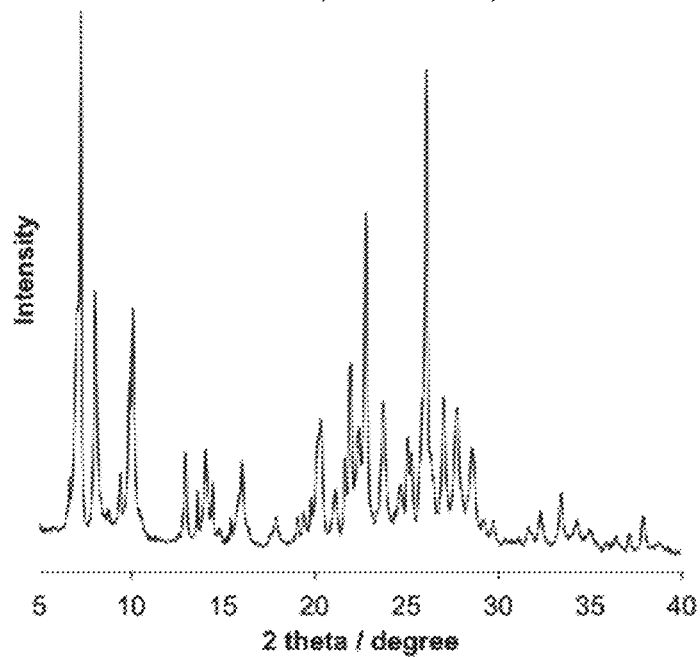
FIG. 5 is an X-ray diffraction pattern of an uncalcined product obtained in Example 2.
Figure 6:
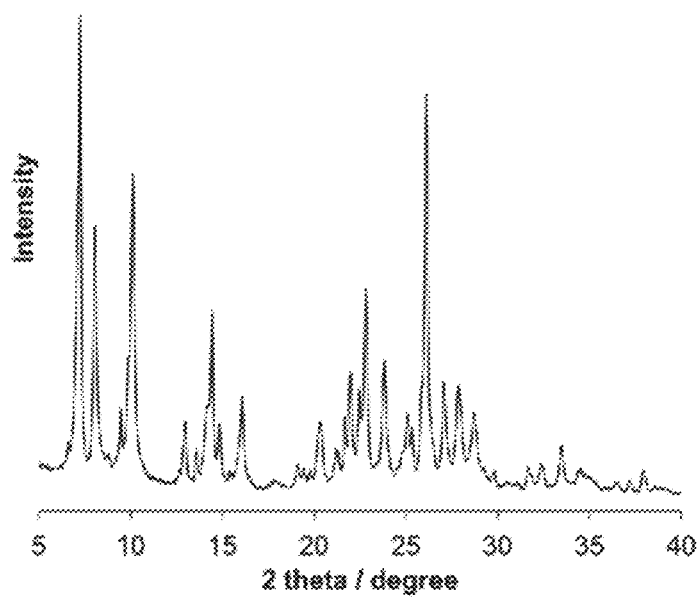
FIG. 6 is an X-ray diffraction pattern of a calcined product obtained in Example 2.
Figure 7:
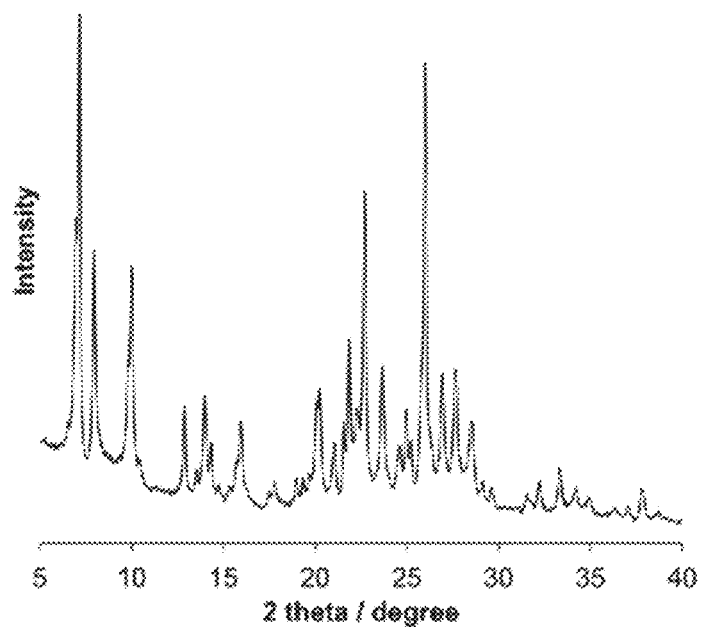
FIG. 7 is an X-ray diffraction pattern of an uncalcined product obtained in Example 3.
Figure 8:
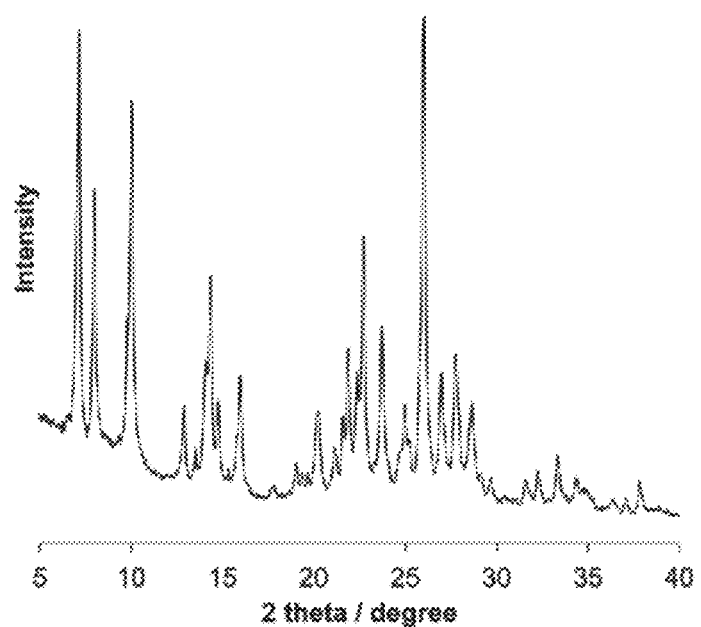
FIG. 8 is an X-ray diffraction pattern of a calcined product obtained in Example 3.
Figure 9:
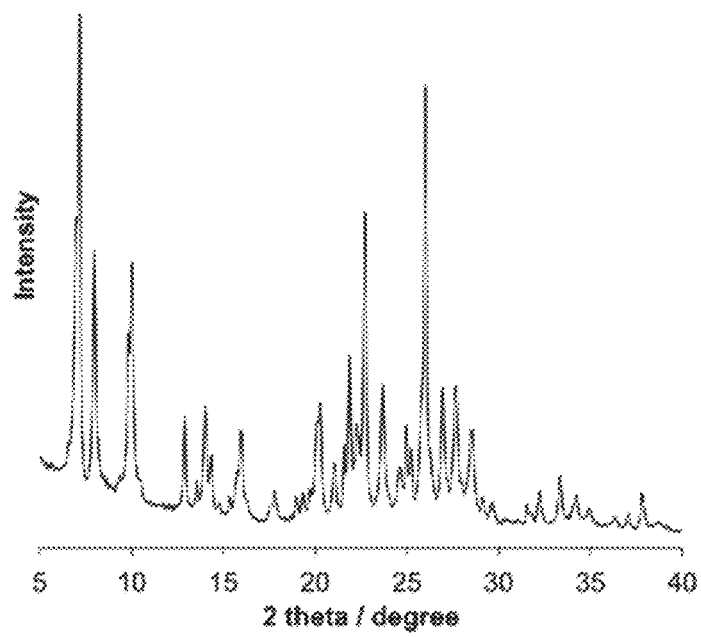
FIG. 9 is an X-ray diffraction pattern of an uncalcined product obtained in Example 4.
Figure 10:
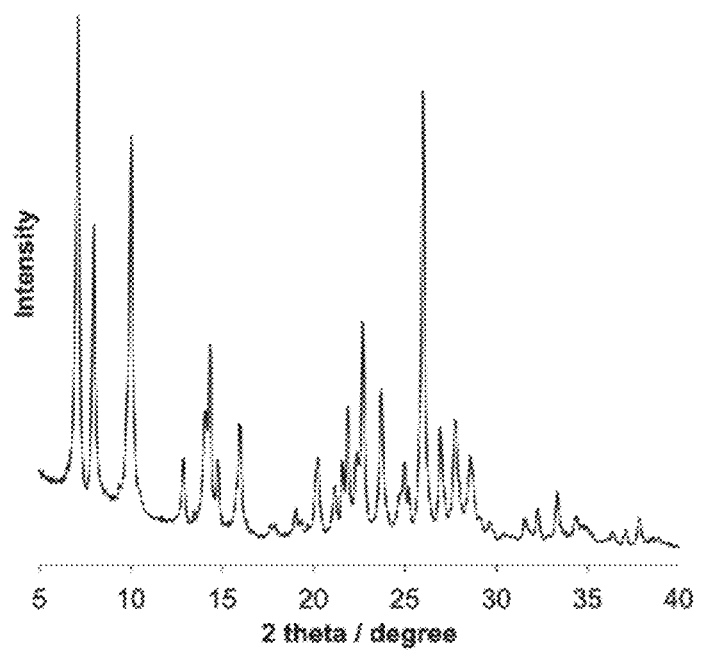
FIG. 10 is an X-ray diffraction pattern of a calcined product obtained in Example 4.
Figure 11:
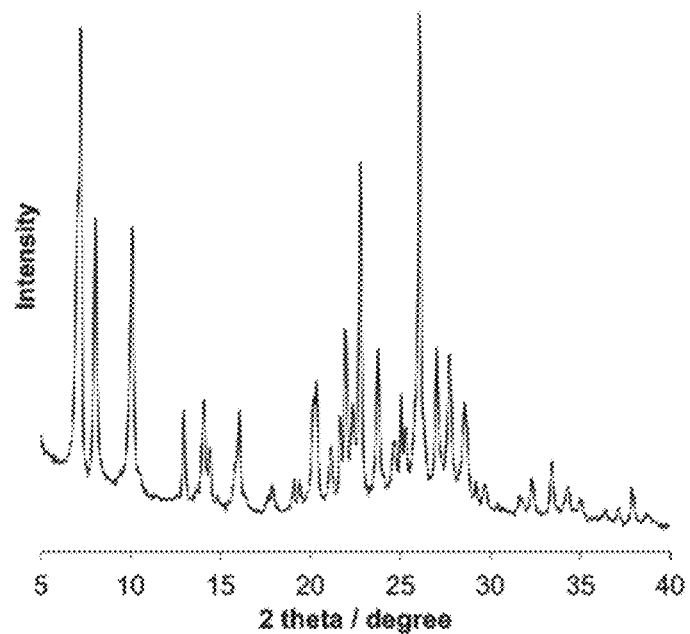
FIG. 11 is an X-ray diffraction pattern of an uncalcined product obtained in Example 5.
Figure 12:
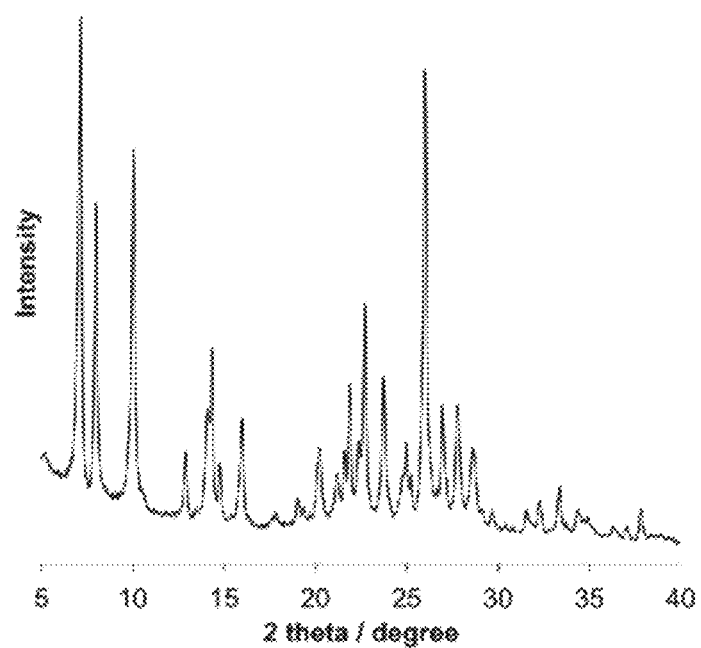
FIG. 12 is an X-ray diffraction pattern of a calcined product obtained in Example 5.

The product synthesized by this production method did not have a crystal structure derived from pillared MCM-22, which is obtained by the existing synthesis method, but had a crystal structure similar to that of MCM-49. FIG. 4 shows an X-ray diffraction pattern obtained after the uncalcined product was calcined in an air atmosphere at 650° C. for 10 hours. The product after calcination was an MWW-type zeolite containing no impurities and had a crystal structure similar to that of 3D MCM-22. Hereinafter, an MWW-type zeolite after calcination in an air atmosphere at 650° C. for 10 hours is referred to as a "calcined MWW-type zeolite". This calcined MWW-type zeolite was subjected to composition analysis. The result showed that $SiO_2/Al_2O_3$ molar ratio was 21.6 and $Na_2O/Al_2O_3$ molar ratio was 0.37.

Examples 2 to 5

Synthesis of MWW-Type Zeolite

Products were obtained as in Example 1 except that the conditions described in Table 1 were employed. X-ray diffraction measurement showed that the obtained uncalcined products were MWW-type zeolites. In the stage of the uncalcined products, the products synthesized by this production method did not have a crystal structure derived from pillared MCM-22, which is obtained by the existing synthesis method, but had a crystal structure similar to that of MCM-49. X-ray diffraction measurement showed that products obtained after the uncalcined products were calcined at 650° C. were MWW-type zeolites and had a crystal structure similar to that of 3D MCM-22. FIGS. 5 to 12 show X-ray diffraction patterns of the uncalcined products and calcined products that were obtained in Examples 2 to 5. The calcined MWW-type zeolites obtained in Examples 2 and 4 were subjected to composition analysis. $SiO_2/Al_2O_3$ molar ratio and $Na_2O/Al_2O_3$ molar ratio are shown in Table 1.

Example 6

Synthesis of MWW-Type Zeolite 0.028 g of sodium aluminate and 0.593 g of a 50 w/v % sodium hydroxide were dissolved into 8.768 g of pure water to prepare an aqueous solution. Subsequently, 0.611 g of fumed silica (Cab-O-Sil, M5) was added gradually and mixed and stirred to prepare a gel having a composition shown in Table 1. This gel had a composition that could produce a mordenite-type zeolite if this gel was solely used to synthesize a zeolite (refer to Comparative Example 5).

Figure 13:
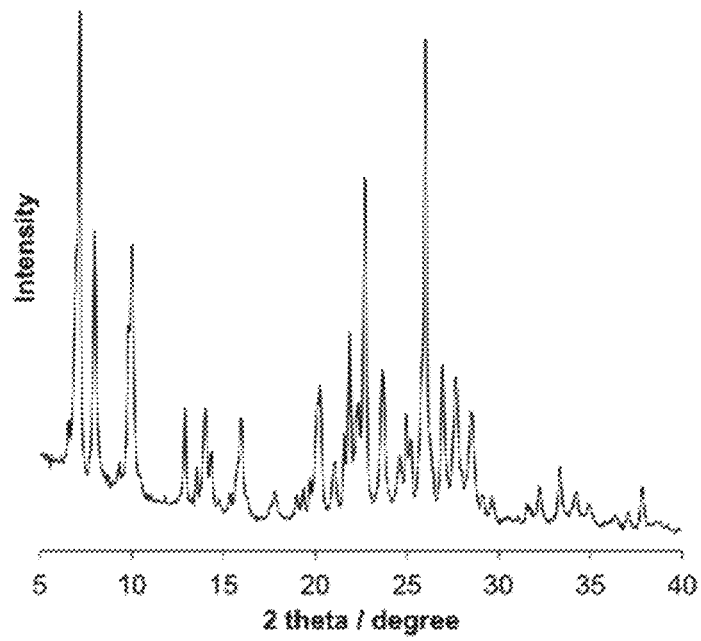
FIG. 13 is an X-ray diffraction pattern of an uncalcined product obtained in Example 6.
Figure 14:
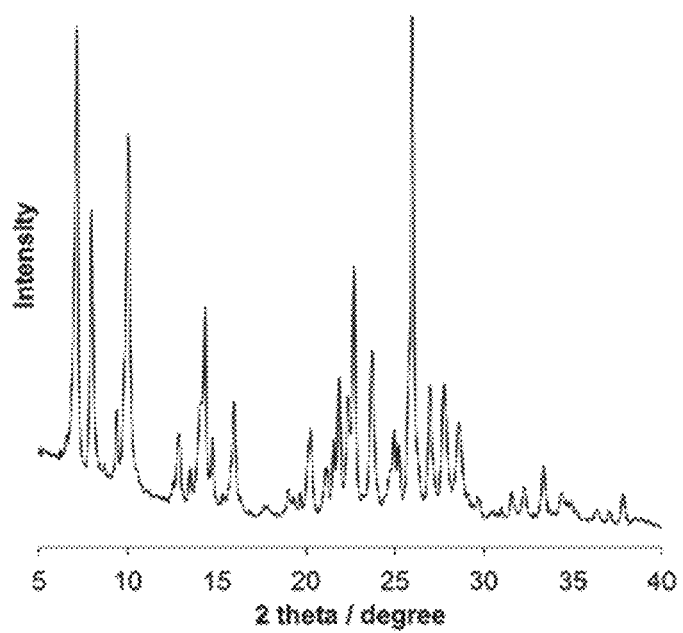
FIG. 14 is an X-ray diffraction pattern of a calcined product obtained in Example 6.

To the gel prepared as described above, 0.05 g of HMI and 0.122 g of the seed crystal calcined product were added. The resulting gel was placed in a 23 cc hermetically sealed container made of stainless steel and allowed to stand under heating at 160° C. for 96 hours under self-generated pressure without stirring. The amount of the seed crystal added was 20% by mass relative to the silica component in the gel. After the hermetically sealed container was cooled, the resulting product was filtered and washed with water to obtain a white powder. FIG. 13 shows an X-ray diffraction pattern of this product. This product was confirmed to be an MWW-type zeolite. One feature of the MWW-type zeolite synthesized by this production method is that, in the stage of the uncalcined product, the product synthesized by this production method did not have a crystal structure derived from pillared MCM-22, which is obtained by the existing synthesis method, but had a crystal structure similar to that of MCM-49. FIG. 14 shows an X-ray diffraction pattern obtained after the uncalcined product was calcined in an air atmosphere at 650° C. for 10 hours. The calcined product was an MWW-type zeolite and had a crystal structure similar to that of 3D MCM-22. The calcined MWW-type zeolite obtained in Example 6 was subjected to composition analysis. $SiO_2/Al_2O_3$ molar ratio and $Na_2O/Al_2O_3$ molar ratio are shown in Table 1.

Examples 7 and 8

Synthesis of MWW-Type Zeolite

Figure 15:
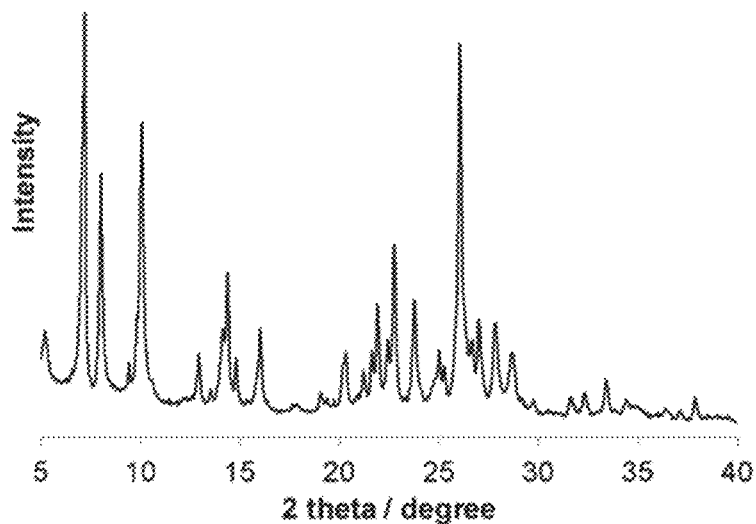
FIG. 15 is an X-ray diffraction pattern of a calcined product obtained in Example 7.
Figure 16:
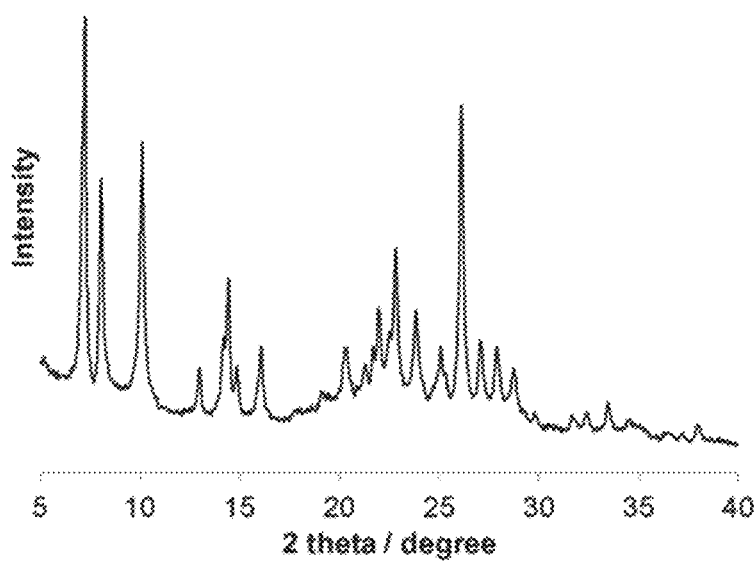
FIG. 16 is an X-ray diffraction pattern of a calcined product obtained in Example 8.

Products were obtained as in Example 1 except that the conditions described in Table 1 were employed. X-ray diffraction measurement showed that the obtained uncalcined products and the calcined products were MWW-type zeolites. FIGS. 15 and 16 show X-ray diffraction patterns of the calcined products. The calcined MWW-type zeolites obtained in Examples 7 and 8 were subjected to composition analysis. $SiO_2/Al_2O_3$ molar ratio and $Na_2O/Al_2O_3$ molar ratio are shown in Table 1.

Comparative Example 1

0.029 g of sodium aluminate and 0.538 g of a 50 w/v % sodium hydroxide were dissolved into 8.822 g of pure water to prepare an aqueous solution. Subsequently, 0.612 g of fumed silica (Cab-O-Sil, M5) was added to the aqueous solution gradually and mixed and stirred to prepare a gel having a composition shown in Table 2. The gel was placed in a 23 cc hermetically sealed container made of stainless steel and allowed to stand under heating at 160° C. for 5 hours under self-generated pressure without stirring. After the hermetically sealed container was cooled, the resulting product was filtered and washed with hot water to obtain a white powder. The results of X-ray diffractometry of this product showed that this product was an amorphous substance.

Comparative Examples 2 to 9

Figure 17:
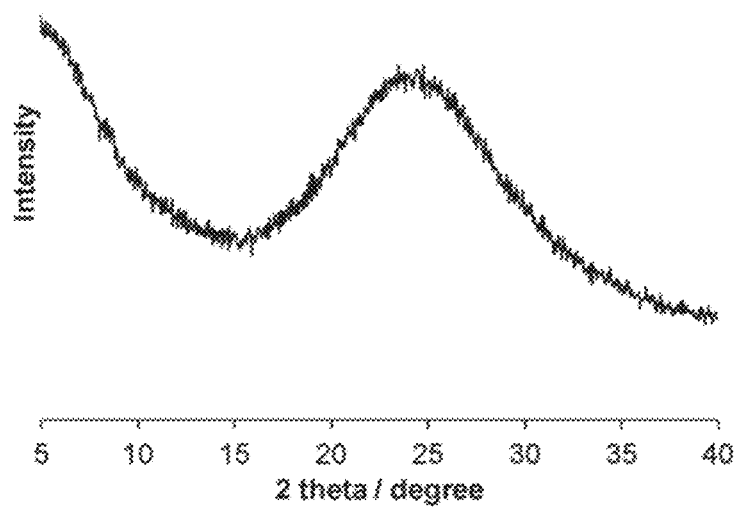
FIG. 17 is an X-ray diffraction pattern of a product obtained in Comparative Example 3.

Products were obtained as in Comparative Example 1 except that the conditions described in Table 2 were employed. X-ray diffraction measurement showed that the obtained products were an amorphous substance or a mordenite-type zeolite. FIG. 17 shows an X-ray diffraction pattern of the product obtained in Comparative Example 3.

Comparative Example 10

0.029 g of sodium aluminate and 0.538 g of a 50 w/v % sodium hydroxide were dissolved into 8.822 g of pure water to prepare an aqueous solution. To the aqueous solution, 0.05 g of HMI was added, and 0.612 g of fumed silica (Cab-O-Sil, M5) was then added to the aqueous solution gradually and mixed and stirred to prepare a gel having a composition shown in Table 2. The gel was placed in a 23 cc hermetically sealed container made of stainless steel and allowed to stand under heating at 160° C. for 5 hours under self-generated pressure without stirring. After the hermetically sealed container was cooled, the resulting product was filtered and washed with hot water to obtain a white powder. The results of X-ray diffractometry of this product showed that the product was an amorphous substance.

Comparative Examples 11 to 20

Figure 18:
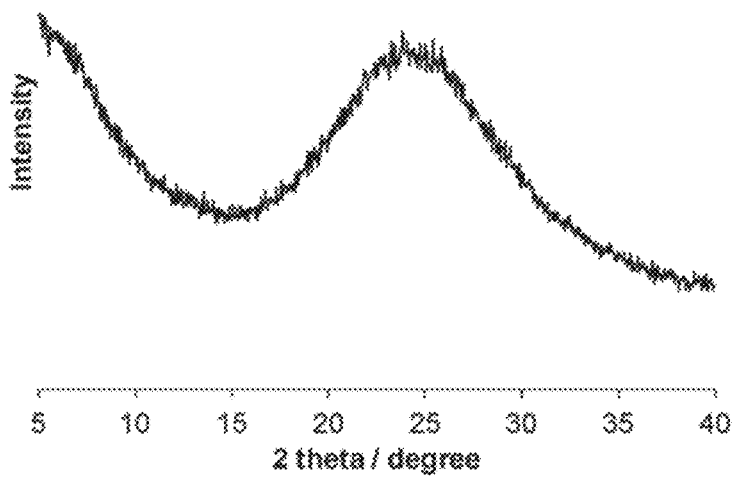
FIG. 18 is an X-ray diffraction pattern of a product obtained in Comparative Example 13.
Figure 19:
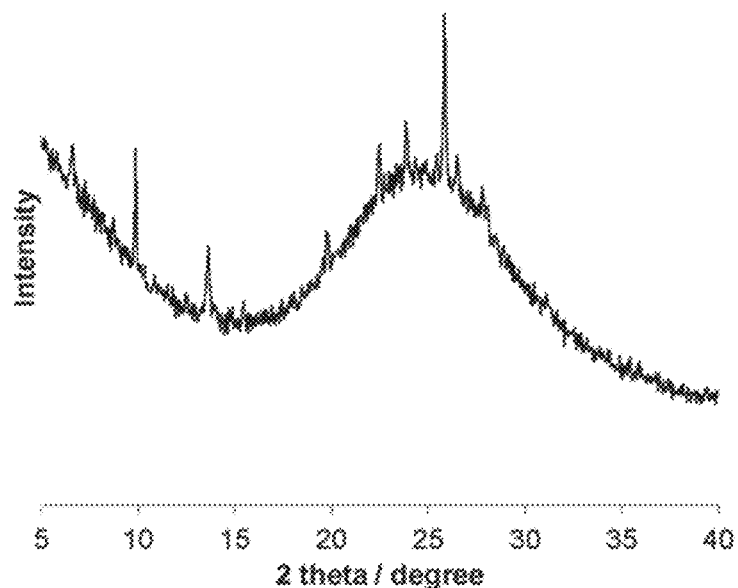
FIG. 19 is an X-ray diffraction pattern of a product obtained in Comparative Example 15.
Figure 20:
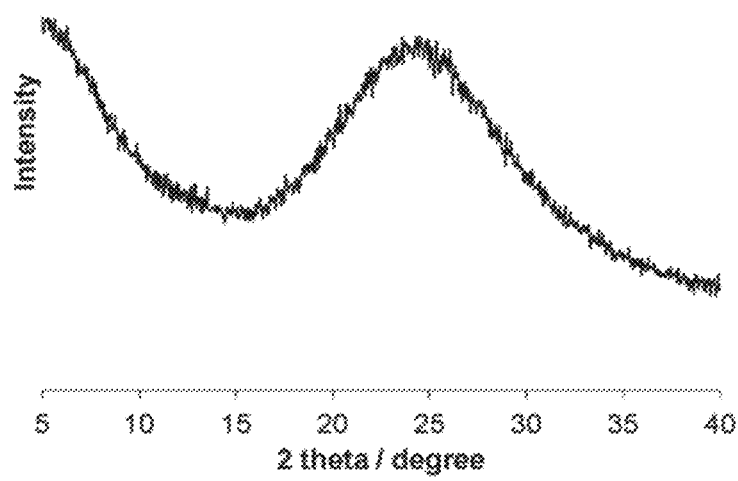
FIG. 20 is an X-ray diffraction pattern of a product obtained in Comparative Example 17.
Figure 21:
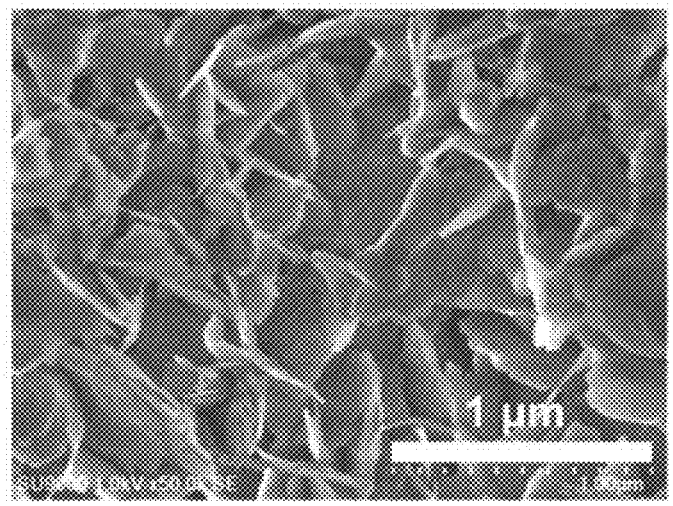
FIG. 21 is a SEM photograph of a calcined MWW-type zeolite for a seed crystal, obtained in Reference Example 1.
Figure 22:
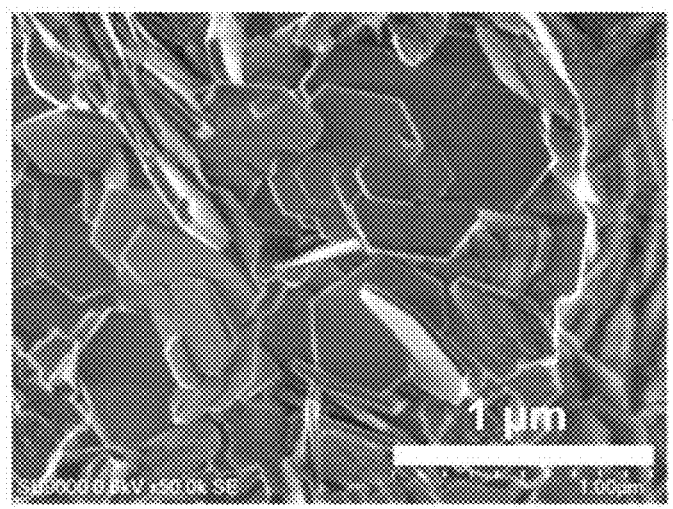
FIG. 22 is a SEM photograph of a calcined product obtained in Example 1.

Products were obtained as in Comparative Example 8 except that the conditions described in Table 2 were employed. X-ray diffraction measurement showed that the obtained products were an amorphous substance, a mordenite-type zeolite having low crystallinity, or an unidentified substance. FIGS. 18, 19, and 20 show X-ray diffraction patterns of the products obtained in Comparative Examples 13, 15, and 17, respectively.

TABLE 1

| Example | Reaction mixture composition (molar retio) | | | | Seed crystal | | Addition Amount (% by mass) | Heating condition | | Stirring Number of rotations (rpm) |
|---|---|---|---|---|---|---|---|---|---|---|
| | SiO$_2$/Al$_2$O$_3$ | Na$_2$O/SiO$_2$ | H$_2$O/SiO$_2$ | HMI/SiO$_2$ | Composition SiO$_2$/Al$_2$O$_3$ | (molar retro) Na$_2$O/Al$_2$O$_3$ | | Temperature (° C) | Time (h) | |
| Reference Example 1 | 30 | 0.147 | 40 | 0.5 | — | — | 0 | 150 | 168 | 20 |
| Example 1 | 100 | 0.25 | 50 | 0.05 | 20 | 0.042 | 20 | 160 | 90 | 0 |
| Example 2 | 100 | 0.25 | 50 | 0.05 | 20 | 0 042 | 10 | 160 | 96 | 0 |
| Example 3 | 100 | 0.25 | 50 | 0.05 | 20 | 0 042 | 5 | 160 | 96 | 0 |
| Example 4 | 100 | 0.25 | 50 | 0.03 | 20 | 0 042 | 20 | 160 | 96 | 0 |
| Example 5 | 100 | 0.25 | 50 | 0.02 | 20 | 0 042 | 20 | 160 | 96 | 0 |
| Example 6 | 100 | 0.275 | 50 | 0.05 | 20 | 0 042 | 20 | 160 | 96 | 0 |
| Example 7 | 60 | 0.2 | 50 | 0.05 | 20 | 0 042 | 20 | 160 | 168 | 0 |
| Example 8 | 60 | 0.15 | 50 | 0.05 | 20 | 0 042 | 20 | 160 | 168 | 0 |

| Example | Product Produced phase | Calcination | SiO$_2$/Al$_2$O$_3$ (molar retro) | Na$_2$O/Al$_2$O$_3$ (molar retro) | Micropore volume (cm$^3$/g) |
|---|---|---|---|---|---|
| Reference Example 1 | MWW | 650° C., 10 h | 20 | 0.042 | 0.1673 |
| Example 1 | MWW | 650° C., 10 h | 21.6 | 0.37 | 0.1944 (0.1965)* |
| Example 2 | MWW | 650° C., 10 h | 20 | 0.33 | 0.1947 |
| Example 3 | MWW | 650° C., 10 h | | | 0.179 |
| Example 4 | MWW | 650° C., 10 h | 19.6 | 0.37 | 0.1974 |
| Example 5 | MWW | 650° C., 10 h | | | 0.1505 |
| Example 6 | MWW | 650° C., 10 h | 18.2 | 0.36 | 0.2032 |
| Example 7 | MWW | 650° C., 10 h | 22.4 | 0.45 | — |
| Example 8 | MWW | 650° C., 10 h | 25.2 | 0.5 | — |

The symbol "—" represents "not measured".
*) The numerical value in the parentheses of Example 1 represents a value of the micropore volume measured after an MWW zeolite of the sodium type was subjected to ammonium ion exchange.

TABLE 2

| Comparative Example | Reaction mixture composition (molar ratio) | | | | Seed crystal Addition amount (% by mass) | Heating condition | | Stirring Number of rotations (rpm) | Product | |
|---|---|---|---|---|---|---|---|---|---|---|
| | SiO$_2$/Al$_2$O$_3$ | Na$_2$O/SiO$_2$ | H$_2$O/SiO$_2$ | HMI/SiO$_2$ | | Temperature (° C.) | Time (h) | | Produced phase | Calcination |
| 1 | 100 | 0.25 | 50 | 0 | 0 | 160 | 5 | 0 | Amorphous | Uncalcined |
| 2 | 100 | 0.25 | 50 | 0 | 0 | 160 | 24 | 0 | Amorphous | Uncalcined |
| 3 | 100 | 0.25 | 50 | 0 | 0 | 160 | 72 | 0 | Amorphous | Uncalcined |
| 4 | 100 | 0.25 | 50 | 0 | 0 | 160 | 692 | 0 | MOR | Uncalcined |
| 5 | 100 | 0.275 | 50 | 0 | 0 | 160 | 692 | 0 | MOR | Uncalcined |
| 6 | 100 | 0.2 | 50 | 0 | 0 | 160 | 168 | 0 | Amorphous | Uncalcined |
| 7 | 60 | 0.2 | 50 | 0 | 0 | 160 | 168 | 0 | Amorphous | Uncalcined |
| 8 | 100 | 0.15 | 50 | 0 | 0 | 160 | 168 | 0 | Amorphous | Uncalcined |
| 9 | 60 | 0.15 | 50 | 0 | 0 | 160 | 168 | 0 | Amorphous | Uncalcined |
| 10 | 100 | 0.25 | 50 | 0.05 | 0 | 160 | 5 | 0 | Amorphous | Uncalcined |
| 11 | 100 | 0.25 | 50 | 0.05 | 0 | 160 | 24 | 0 | Amorphous | Uncalcined |
| 12 | 100 | 0.25 | 50 | 0.05 | 0 | 160 | 72 | 0 | Amorphous | Uncalcined |
| 13 | 100 | 0.25 | 50 | 0.05 | 0 | 160 | 96 | 0 | Amorphous | Uncalcined |
| 14 | 100 | 0.25 | 50 | 0.05 | 0 | 160 | 168 | 0 | Unidentified substance | Uncalcined |
| 15 | 100 | 0.275 | 50 | 0.05 | 0 | 160 | 96 | 0 | Unidentified substance | Uncalcined |
| 16 | 100 | 0.275 | 50 | 0.05 | 0 | 160 | 168 | 0 | MOR (low crystallinity) | Uncalcined |
| 17 | 100 | 0.25 | 50 | 0.03 | 0 | 160 | 96 | 0 | Amorphous | Uncalcined |
| 18 | 100 | 0.25 | 50 | 0.03 | 0 | 160 | 168 | 0 | Unidentified substance | Uncalcined |

TABLE 2-continued

| Comparative Example | Reaction mixture composition (molar ratio) | | | | Seed crystal Addition amount (% by mass) | Heating condition | | Stirring Number of rotations (rpm) | Product | |
|---|---|---|---|---|---|---|---|---|---|---|
| | $SiO_2/Al_2O_3$ | $Na_2O/SiO_2$ | $H_2O/SiO_2$ | $HMI/SiO_2$ | | Temperature (°C.) | Time (h) | | Produced phase | Calcination |
| 19 | 100 | 0.275 | 50 | 0.03 | 0 | 160 | 96 | 0 | Unidentified substance | Uncalcined |
| 20 | 100 | 0.275 | 50 | 0.03 | 0 | 160 | 168 | 0 | MOR (low crystallinity) | Uncalcined |

As is apparent from the comparison between Table 1 and Table 2, MWW-type zeolites can be obtained by using a specific MWW-type zeolite as a seed crystal, adding this seed crystal to a reaction mixture having a specific composition, and performing crystallization, as in Examples 1 to 8. An amorphous substance, an unidentified substance, or a zeolite other than an MWW-type zeolite is produced in the cases where neither a seed crystal nor HMI is used or in the cases where no seed crystal is contained and the amount of HMI added is smaller than the amount necessary for synthesizing a seed crystal in the related art, as in Comparative Examples 1 to 20.

As described above, in the ICP-AES composition analysis, $Na_2O/Al_2O_3$ molar ratio of each of the MWW-type zeolites (calcined products) obtained by the present production method is 0.33 or more, as shown in Table 1. On the other hand, $Na_2O/Al_2O_3$ molar ratio of the MWW-type zeolite seed crystal (calcined product) obtained by the existing method is 0.042 or less. Thus, $Na_2O/Al_2O_3$ molar ratios of the products and the seed crystal differ according to production methods.

Measurement and evaluation of the MWW-type zeolites obtained in Examples and Reference Example were performed by using the measuring instruments described above. The results will be described below.

[Microscopic Observation]

Figure 23:
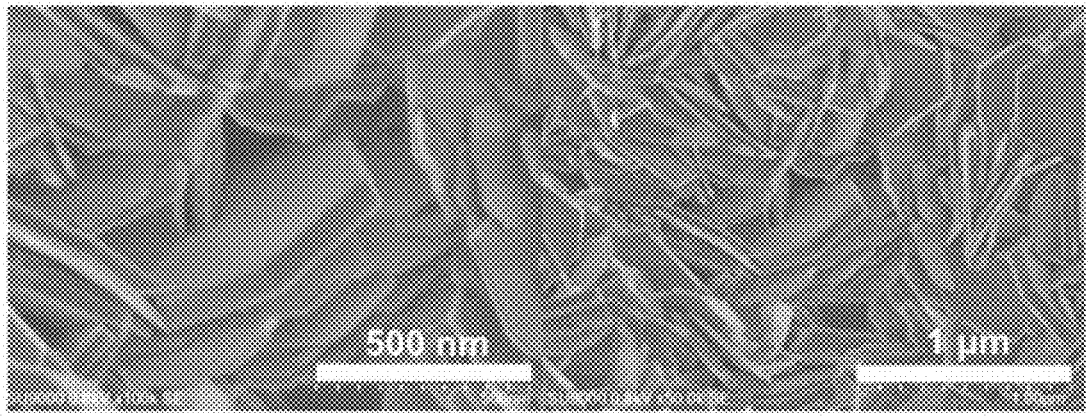
FIG. 23 is a SEM photograph of an uncalcined product obtained in Example 1.
Figure 24:
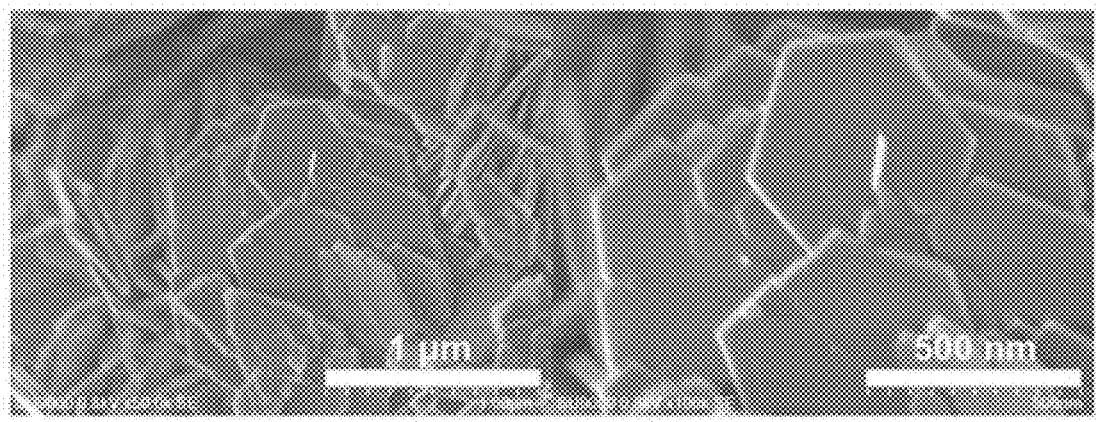
FIG. 24 is a SEM photograph of a calcined product after ammonium ion exchange, the calcined product being obtained in Example 1.
Figure 25:
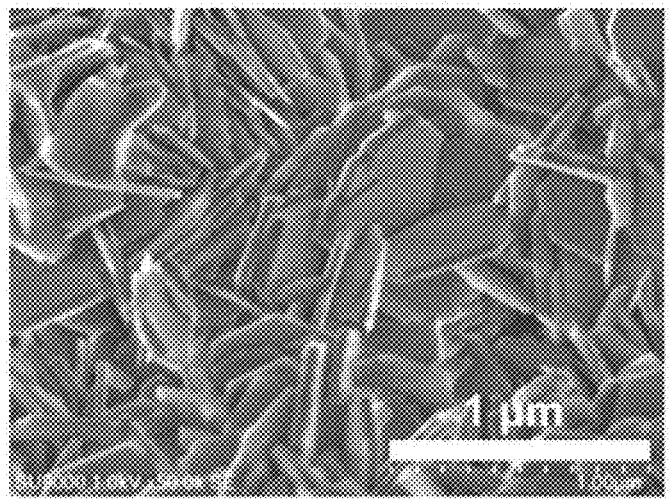
FIG. 25 is a SEM photograph of a calcined product obtained in Example 2.
Figure 26:
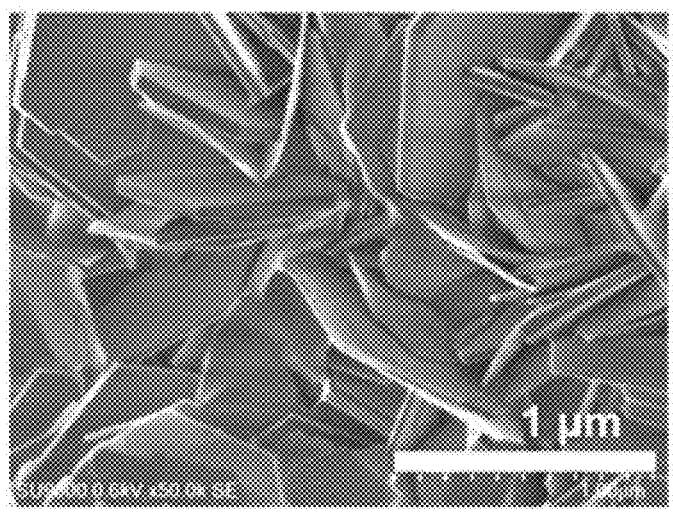
FIG. 26 is a SEM photograph of a calcined product obtained in Example 3.
Figure 27:
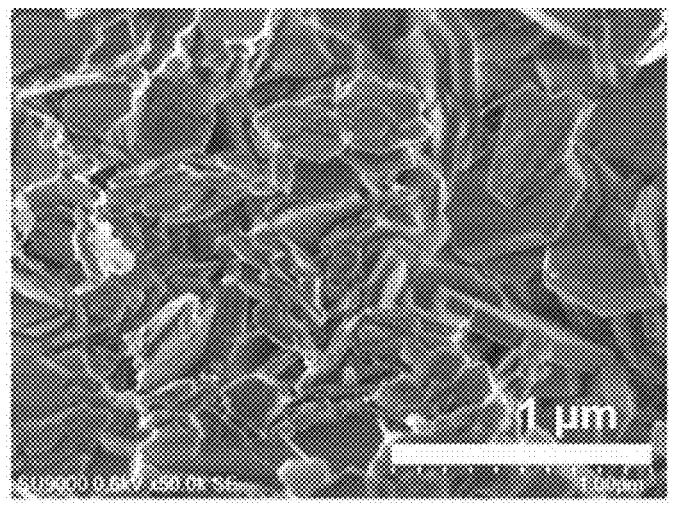
FIG. 27 is a SEM photograph of a calcined product obtained in Example 4.
Figure 28:
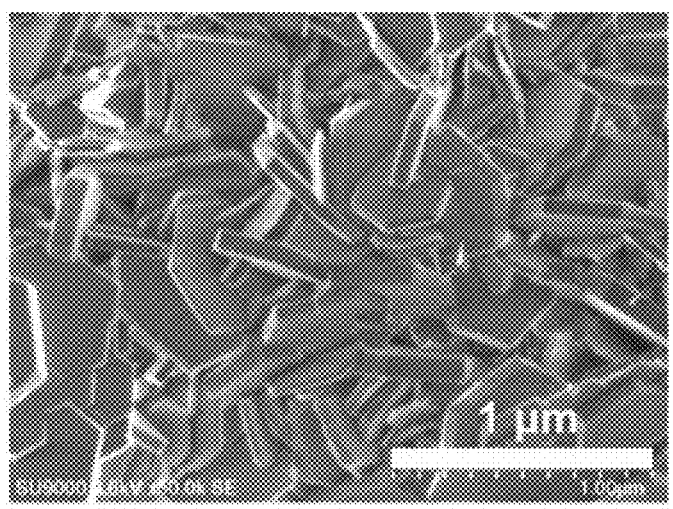
FIG. 28 is a SEM photograph of a calcined product obtained in Example 5.

The MWW-type zeolites obtained in Examples were observed with an ultra-high resolution field-emission scanning electron microscope. As an example, FIGS. 21 to 28 show electron micrographs of the MWW-type zeolite seed crystal (Reference Example 1) obtained by the existing method and the MWW-type zeolites (Examples 1 to 5) obtained by the present production method. As is apparent from the comparison between FIG. 21 and FIGS. 22 to 28, the seed crystal of Reference Example 1 obtained by the related art does not have a hexagonal plate-like shape, whereas the MWW-type zeolites (calcined products) of Examples each show a clear hexagonal plate-like crystal form. From the image of the MWW-type zeolite of Example 1, the length of one side of the resulting product was about 160 to 320 nm. The thickness was about 20 to 60 nm. As shown in FIGS. 23 and 24, each of the uncalcined product of Example 1 and a product obtained by subjecting the calcined product of Example 1 to ion exchange with ammonium ions by the method described below similarly also had a clear hexagonal plate-like crystal form.

[Measurement of Micropore Volume by $N_2$ Adsorption-Desorption Method]

The micropore volumes of the (calcined) MWW-type zeolites obtained in Examples and Reference Example 1 were measured by the $N_2$ adsorption-desorption method using the above instrument. As shown in Table 1, the MWW-type zeolites (calcined products) obtained by the present production method have a micropore volume of 0.1505 $cm^3/g$ or more and 0.2032 $cm^3/g$ or less, whereas the MWW-type zeolite seed crystal (calcined product) of Reference Example 1 obtained by the existing method has a micropore volume of 0.1673 $cm^3/g$. The MWW-type zeolites according to the present invention, except for Example 5, have microscopic volume higher than the seed crystal of Reference Example 1. As a pretreatment of the $N_2$ adsorption-desorption method, all the measurement samples were evacuated at 400° C. for at least 8 hours.

With regard to the calcined MWW-type zeolite obtained in Example 1, the micropore volume after ion exchange for the ammonium type was also measured. The value was 0.1965 $cm^3/g$. The ammonium ion exchange was conducted by the method described below. The resulting ion-exchanged product was evacuated at 400° C. for at least 8 hours as the pretreatment prior to adsorption. The micropore volume was then determined by the $N_2$ adsorption-desorption method using a BELSORP-mini manufactured by MicrotracBEL Corp.

[Solid-State $^{27}Al$ MAS NMR Measurement]

<$NH_4$ Ion Exchange of MWW-Type Zeolite>

An aqueous ammonia was added to an aqueous ammonium chloride solution to prepare a 1 mol/L aqueous ammonium chloride solution having a pH of about 7.03. The calcined MWW-type zeolite obtained in Example 1 was used as a raw material, and about 1.95 g of the MWW-type zeolite was dispersed in 500 mL of the 1 mol/L aqueous ammonium chloride solution. This dispersion liquid was stirred at room temperature for 30 minutes to perform ion exchange. Subsequently, the MWW-type zeolite was separated by filtration. The procedure of ion exchange and filtration was further repeated two times, and the resulting MWW-type zeolite was then washed with water and dried at 60° C. Thus, an $NH_4$-exchanged MWW-type zeolite was obtained. Among MWW-type zeolites of the ammonium type obtained as described above, $SiO_2/Al_2O_3$ molar ratio of the MWW-type zeolite of the ammonium type of Example 1 was measured with the above-mentioned ICP measuring instrument. The value was 20.6. $Na_2O/Al_2O_3$ molar ratio of the MWW-type zeolite of the ammonium type of Example 1 was measured with the ICP measuring instrument. The value was 0.003.

An $^{27}Al$ MAS NMR (magic angle spinning nuclear magnetic resonance) spectrum of an MWW-type zeolite was obtained by the following method.

A 4 mm zirconia rotor was filled with a sample and introduced into a probe. Tuning in accordance with an $^{27}Al$ resonance frequency, i.e., 156.388 MHz, which corresponds to a 1H resonance frequency, i.e., 600.130 MHz, was conducted. The sample tube was tilted at 54.73° (magic angle)

with respect to the external magnetic field and rotated at a high speed at 13 kHz. Pulses of radio waves were applied, and the obtained FID (free induction decay) signals were Fourier-transformed to obtain an NMR spectrum. Resonance peaks having a chemical shift in the range of 40 to 80 ppm, with reference to aluminum nitrate of 1,000 ppm, were regarded as peaks attributable to tetracoordinate Al. Resonance peaks having a chemical shift in the range of −10 to 10 ppm were regarded as peaks attributable to hexacoordinate Al.

Figure 29:
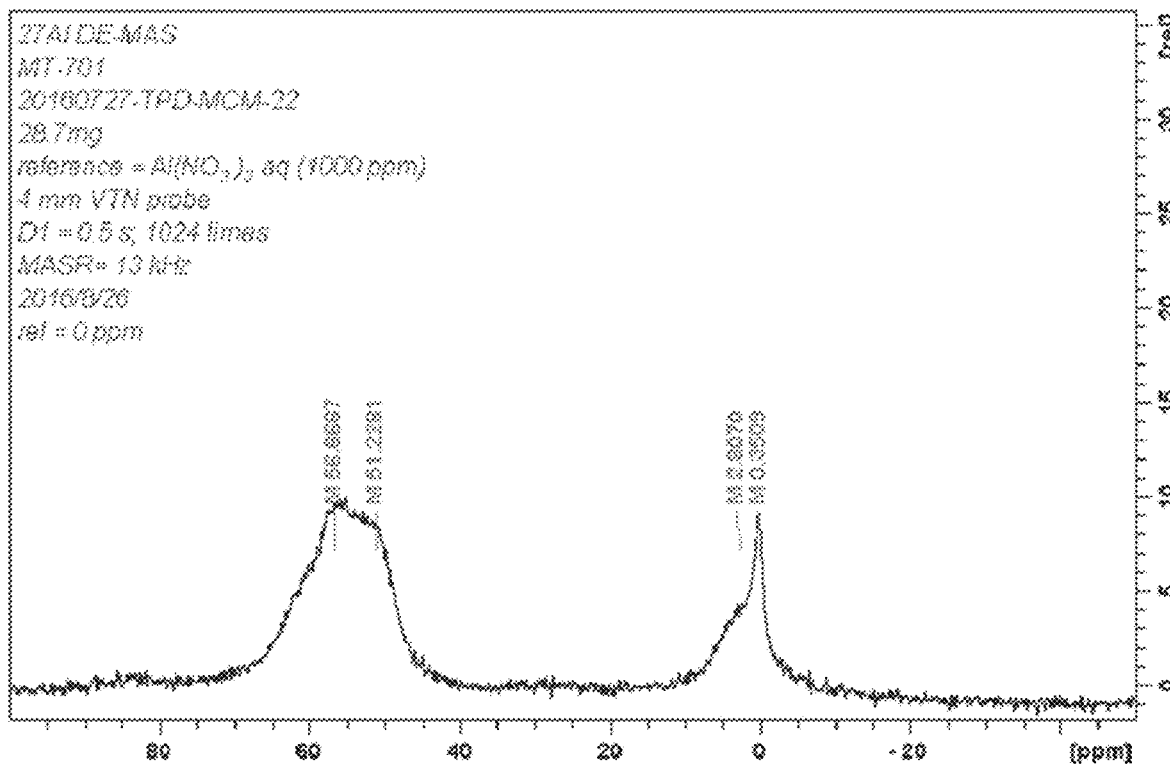
FIG. 29 is an $^{27}Al$ MAS NMR chart of a calcined seed crystal obtained in Reference Example 1.
Figure 30:
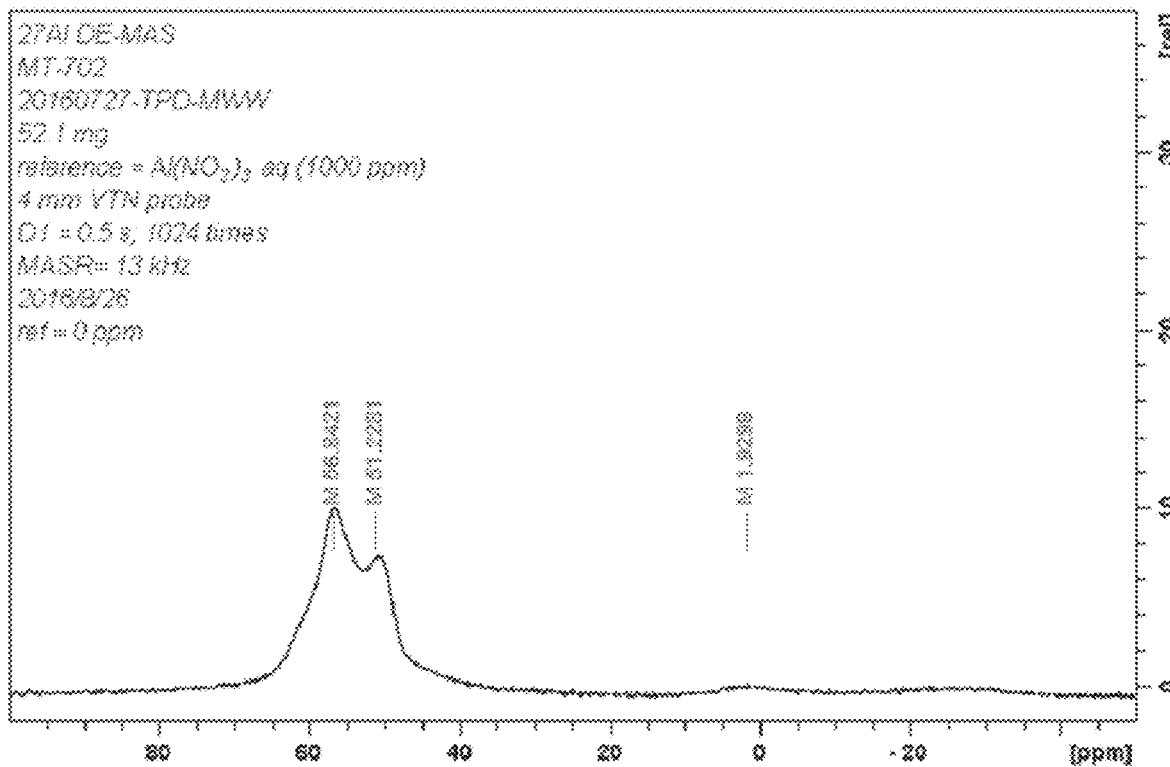
FIG. 30 is an $^{27}Al$ MAS NMR chart of a calcined product after ammonium ion exchange, the calcined product being obtained in Example 1.

FIG. 29 shows a solid-state $^{27}$Al MAS NMR spectrum of the MWW-type zeolite seed crystal (Reference Example 1) obtained by the existing method. FIG. 30 shows a solid-state $^{27}$Al MAS NMR spectrum of the MWW-type zeolite of Example 1.

As shown in FIG. 30, in the MWW-type zeolite prepared by calcining the MWW-type zeolite obtained in Example 1 and then performing NH$_4$ exchange, peaks (chemical shift: 40 to 80 ppm) attributable to tetracoordinate aluminum were solely observed, and no peak attributable to hexacoordinate aluminum was observed.

In contrast, as shown in FIG. 29, in the solid-state $^{27}$Al MAS NMR spectrum of the MWW-type zeolite seed crystal, in addition to peaks (chemical shift: 40 to 80 ppm) attributable to tetracoordinate aluminum, a peak (chemical shift: 0 ppm) attributable to hexacoordinate aluminum was observed.

Furthermore, solid-state $^{27}$Al MAS NMR spectra of the calcined MWW-type zeolites obtained in Examples 2 to 8 were also similarly evaluated. As the result, peaks attributable to tetracoordinate aluminum were solely observed, whereas no peak attributable to hexacoordinate aluminum was observed.

[Amount of BrøNsted Acid Sites]

The amount of Brønsted acid sites was measured by the method described in J. Phys. Chem. B, 109, (40) pp. 18749-18757 (2005). Specifically, the measurement was performed as follows.

In NH$_3$-IRMS-TPD, the MWW-type zeolite calcined product obtained in Example 1 was subjected to NH$_4$ exchange by the method described above. The amount of Brønsted acid sites was measured in an apparatus as follows. About 7 mg of the zeolite was compression-molded so as to have a disc shape with a diameter of 10 mm. The resulting molded sample was then placed in a mesh-type sample holder provided with an IRMS-TPD apparatus manufactured by MicrotracBEL Corp. and set in the apparatus. Oxygen was allowed to flow at a flow rate of 50 cm$^3$ min$^{-1}$ (standard state volume) and the temperature was increased to 823 K. The temperature of 823 K was maintained for 1 hour. Then, vacuum evacuation was performed for 10 minutes while the temperature was maintained at 823 K. The temperature was decreased to 343 K while the vacuum was maintained. Subsequently, helium was allowed to flow at a flow rate of 120 cm$^3$ min$^{-1}$ (standard state volume). Evacuation was performed from an outlet with a vacuum pump so as to maintain a pressure of 6.0 kPa inside the system. The temperature was increased to 803 K at a rate of 2 K min$^{-1}$. During the temperature increase, an infrared spectrum was obtained at a frequency of once per 1 K.

Subsequently, the temperature was decreased to 343 K while helium continued to flow. After degassing, 13 kPa of ammonia was introduced at 343 K and this state was held for 30 minutes. After degassing was performed for 180 minutes, helium was allowed to flow at a flow rate of 120 cm$^3$ min$^{-1}$ (standard state volume). Evacuation was performed from the outlet with the vacuum pump so as to maintain a pressure of 6.0 kPa inside the system. The temperature was increased to 803 K at a rate of 2 K min$^{-1}$. During the temperature increase, a mass spectrum was constantly recorded and an infrared spectrum was simultaneously measured at a frequency of once per 1 K.

After the completion of the temperature increase, an ammonia-helium gas mixture of a known concentration was allowed to flow. On the basis of the response of a mass spectrometer at this time, the mass spectrum was converted into a gas-phase ammonia concentration. A function obtained by plotting the gas-phase ammonia concentration with respect to the temperature was defined as M(T). Here, T represents temperature.

After the completion of the measurement, the sample was removed and weighed. Meanwhile, results obtained by plotting a value determined by subtracting an infrared absorbance before ammonia adsorption from an infrared absorbance after ammonia adsorption for each wave number of infrared-ray with respect to the wave number were defined as an infrared difference spectrum. A function obtained by plotting, with respect to the temperature, a value determined by multiplying the derivative of the peak area at 1,260 to 1,330 cm$^{-1}$ of the infrared difference spectrum with respect to the temperature by −1 is defined as L(T). A function obtained by plotting, with respect to the temperature, a value determined by multiplying the derivative of the peak area at 1,420 to 1,500 cm$^{-1}$ with respect to the temperature by −1 is defined as B(T). Values of x and y were selected by trial and error such that z in the following expression becomes the minimum.

$$z = \sum_{T=343K}^{803K} \{xL(T) + yB(T) - M(T)\}^2$$

The strength distribution of the Brønsted acid sites was determined from the obtained yB(T) by the method described in Appl. Catal. A: Gen., 340, (1) pp. 76-86 (2008). As the result, in the MWW-type zeolite obtained by the present production method, the amount of Brønsted acid sites with an adsorption heat of ammonia of 106 kJ/mol or more was 0.76 mmol/g. With regard to the seed crystal (calcined product) of Reference Example 1 obtained by the existing synthesis method, the amount of Brønsted acid sites was similarly measured. As the result, in contrast, the amount of Brønsted acid sites with an adsorption heat of ammonia of 106 kJ/mol or more was 0.34 mmol/g. Accordingly, the amount of Brønsted acid sites of the MWW-type zeolite obtained by the present production method is higher than that of the seed crystal by about 2 times. According to the above results, the MWW-type zeolite of Example 1 is considered to have a large amount of Brønsted acid sites when the zeolite is converted into a proton type and to have high catalytic activity compared with Reference Example 1.

With regard to the calcined MWW-type zeolites obtained in Examples 2 to 8, the amount of Brønsted acid sites with an adsorption heat of ammonia of 106 kJ/mol or more was measured as in Example 1. According to the results, the amount of Brønsted acid sites was 0.5 mmol/g or more.

[Cracking Reaction of Cumene]

With regard to the MWW-type zeolite prepared by subjecting the calcined product of the MWW-type zeolite obtained in Example 1 to NH$_4$ exchange by the method described in <NH$_4$ ion exchange of MWW-type zeolite> and the seed crystal (calcined product) of Reference Example 1 obtained by the related art, the catalytic activity in cracking reaction of cumene was evaluated by the following procedure.

The catalytic reaction in this Example was carried out by using an atmospheric pressure fixed-bed flow reactor. In a Pyrex (registered trademark) tube having an inner diameter of 4 mm, about 10 mg of a zeolite sample was fixed by using quartz glass wool. Helium was allowed to pass through a tube filled with activated alumina cooled at 77 K and then pass through the Pyrex tube. This method allowed helium to pass through the zeolite sample layer at a flow rate of 37 μmol/s. While helium was allowed to flow, the temperature of the zeolite sample was increased to 530° C. and held at 530° C. for 1 hour. Subsequently, a vapor of 7.2 μmol of cumene was introduced into the helium flow and allowed to pass through the zeolite sample layer at 250° C. Cumene was introduced by the following method. An inlet equipped with a septum made of silicon rubber was provided on the upstream of the Pyrex tube filled with the zeolite sample. The inlet was heated to about 393 K, and 1 mm³ of reagent special grade liquid cumene manufactured by FUJIFILM Wako Pure Chemical Corporation was quickly injected from the inlet with a micro-syringe. An outlet of the Pyrex tube was connected to a GC-8A gas chromatograph manufactured by Shimadzu Corporation through a column filled with silicone SE30 manufactured by GL Science Inc. Substances discharged from this outlet were separated in the column, then reach a detector (flame ionization detector) with the lapse of a retardation time particular to each of the substances, and were electrically detected. Propene, benzene, cumene, and the like were quantified with reference to the response when 7.2 μmol of cumene was injected from the outlet on the downstream of the Pyrex tube. This experiment provided the results shown in Table 3.

TABLE 3

| Example | Amount of sample (mg) | Material balance (%) | Amount of recovered cumene (μmol) | Cumene conversion rate (%) | Amount of loss of cumene per amount of zeolite sample mmol/kg |
|---|---|---|---|---|---|
| Reference Example 1 | 10 | 97.6 | 6.74 | 6.02 | 43 |
| Example 1 | 11.1 | 87.5 | 5.02 | 30.1 | 194 |

As shown in Table 3, in each of the cases where the two types of zeolite samples were used, the amount of cumene decreased, benzene and propylene were produced, and other products were hardly observed. The material balance was 87.5% or 97.6%, and these results showed that a small amount of a substance was changed to an undetectable component. This is presumably because a polymerized product was produced and remained on the catalyst. The catalytic activity was calculated by dividing the amount of loss of cumene by the mass of the zeolite sample. Comparing the cumene conversion rate per amount of zeolite sample, the MWW-type zeolite prepared by calcining the MWW-type zeolite obtained in Example 1 and then subjecting the calcined MWW-type zeolite to $NH_4$ exchange exhibited a catalytic activity about five times that of the seed crystal (calcined product) obtained by the related art in Reference Example 1. It is believed that decomposition (dealkylation) of cumene proceeds on Brønsted acid sites. Accordingly, a high cumene decomposition activity in an MWW-type zeolite means that the MWW-type zeolite has a large number of active Brønsted acid sites suitable for use of the MWW-type zeolite.

The invention claimed is:

1. An MWW-type zeolite wherein a ratio (B/A) of a peak intensity (B) attributable to tetracoordinate aluminum to a peak intensity (A) attributable to hexacoordinate aluminum is 2 or more in $^{27}$Al MAS NMR as measured from an ammonium form of the MWW-type zeolite, wherein the ratio (B/A) refers to a peak height ratio in the NMR chart, wherein the MWW-type zeolite is a calcined product after synthesis, and wherein the $^{27}$Al MAS NMR is measured directly from the MWW-type zeolite in a case where the MWW-type zeolite is the ammonium form or measured after the MWW-type zeolite is converted into the ammonium form in a case where the MWW-type zeolite is not in the ammonium form.

2. The MWW-type zeolite according to claim 1, wherein an amount of Brønsted acid sites with a adsorption heat of ammonia of 106 kJ/mol or more is 0.5 mmol/g or more.

3. The MWW-type zeolite according to claim 1, wherein a micropore volume is 0.07 cm³/g or more and 0.2530 cm³/g or less.

4. The MWW-type zeolite according to claim 1, wherein a $SiO_2/Al_2O_3$ molar ratio is 17 or more and 37 or less.

5. The MWW-type zeolite according to claim 1, wherein when the MWW-type zeolite is subjected to X-ray diffraction measurement, a peak is observed in at least one range below:

2θ=6.4° to 7.4°, 13.5° to 14.5°, 24.1° to 25.1°, 24.7 to 25.7°, 27.1 to 28.1°, 28.0° to 29.0°, 28.6° to 29.6°, and 29.1° to 30.1°.

6. The MWW-type zeolite according to claim 1, having a hexagonal plate-like shape.

7. A cracking catalyst for cumene, the cracking catalyst comprising the MWW-type zeolite according to claim 1.

8. A method for producing the MWW-type zeolite according to claim 1, the method comprising a step of carrying out hydrothermal synthesis in the presence of a seed crystal of the MWW-type zeolite containing no organic structure-directing agent, and a reaction mixture containing a silica source, an alumina source, an alkali source, an organic structure-directing agent, and water, wherein the reaction mixture satisfies a molar ratio below:

$X/SiO_2<0.15$ (where X denotes the number of moles of the organic structure-directing agent).

9. The production method according to claim 8, wherein the reaction mixture used has a composition represented by molar ratios below:

$SiO_2/Al_2O_3$=5 or more and 200 or less;

$Na_2O/SiO_2$=0.05 or more and 0.5 or less;

$H_2O/SiO_2$=5 or more and 200 or less; and $X/SiO_2$=0.01 or more and less than 0.15 (where X denotes the number of moles of the organic structure-directing agent).

10. The production method according to claim 8, wherein the seed crystal used has a $SiO_2/Al_2O_3$ molar ratio of 10 to 40.

11. The production method according to claim 8, wherein the seed crystal is used in a ratio of 1% by mass or more and 50% by mass or less relative to $SiO_2$ in the reaction mixture.

12. The production method according to claim 8, wherein the hydrothermal synthesis is carried out under heating at 100° C. to 180° C.

13. The production method according to claim 8, wherein the organic structure-directing agent is hexamethyleneimine.

* * * * *